(12) United States Patent
Schreiber

(10) Patent No.: US 10,405,942 B2
(45) Date of Patent: *Sep. 10, 2019

(54) AIRFRAME SYSTEM AND METHOD OF CONTROLLING AIRFLOW

(71) Applicant: SLD Technology, Inc., Portland, OR (US)

(72) Inventor: Kevin Joseph Schreiber, Happy Valley, OR (US)

(73) Assignee: SLD Technology, Inc., Portland, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/905,214

(22) Filed: Feb. 26, 2018

(65) Prior Publication Data

US 2018/0256280 A1  Sep. 13, 2018

Related U.S. Application Data

(63) Continuation of application No. 15/288,232, filed on Oct. 7, 2016, now Pat. No. 9,903,115.

(Continued)

(51) Int. Cl.
*A61B 90/35* (2016.01)
*F21V 21/08* (2006.01)
(Continued)

(52) U.S. Cl.
CPC .............. *A61B 90/35* (2016.02); *E04B 9/003* (2013.01); *E04B 9/006* (2013.01); *E04B 9/02* (2013.01); *E04B 9/064* (2013.01); *F21V 15/013* (2013.01); *F21V 17/164* (2013.01); *F21V 21/048* (2013.01); *F21V 21/088* (2013.01); *F24F 3/06* (2013.01); *F24F 3/1603* (2013.01); *F24F 3/1607* (2013.01); *F24F 13/28* (2013.01); *E04H 3/08* (2013.01); *F21S 8/043* (2013.01); *F21V 5/04* (2013.01); *F21W 2131/205* (2013.01)

(58) Field of Classification Search
CPC ........ A61B 90/35; F34F 3/1603; E04B 9/006; E04B 9/02; F21S 8/043; F21V 21/088; F21V 5/04; E04H 3/08; F21W 2131/205
See application file for complete search history.

(56) References Cited

U.S. PATENT DOCUMENTS 2,621,579 A  12/1952  Person
2,845,855 A   8/1958  Burns
(Continued)

FOREIGN PATENT DOCUMENTS

| CA | 2951300 A1 * | 6/2017 | .............. F21S 8/026 |
|----|---|---|---|
| EP | 2472178 A1 * | 7/2012 | .............. F21S 8/026 |
| WO | WO-2007119009 A1 * | 10/2007 | .............. B60P 3/005 |

*Primary Examiner* — Jeanette E Chapman
(74) *Attorney, Agent, or Firm* — Barta, Jones & Foley, P.C.

(57) ABSTRACT

An air frame system includes a frame body defining one or more openings, a plurality of air passages along an inner periphery of the one or more openings, and an airframe grid coupled to the frame body. The airframe grid includes at least one wireway channel therein and a wireway channel cover clip is removably coupled to the at least one wireway channel. The air frame system also includes a light assembly removably coupled to the airframe grid, and a retainer clip removably coupled to the airframe grid. The airframe grid retains the light assembly within the airframe grid.

20 Claims, 30 Drawing Sheets

Related U.S. Application Data

(60) Provisional application No. 62/238,601, filed on Oct. 7, 2015.

(51) Int. Cl.

| | | |
|---|---|---|
| *E04B 9/02* | (2006.01) | |
| *F24F 3/16* | (2006.01) | |
| *E04B 9/00* | (2006.01) | |
| *F21V 15/01* | (2006.01) | |
| *F21V 17/16* | (2006.01) | |
| *F21V 21/04* | (2006.01) | |
| *F24F 3/06* | (2006.01) | |
| *F21V 5/04* | (2006.01) | |
| *F21V 21/088* | (2006.01) | |
| *E04B 9/06* | (2006.01) | |
| *F24F 13/28* | (2006.01) | |
| *F21S 8/04* | (2006.01) | |
| *E04H 3/08* | (2006.01) | |
| *F21W 131/205* | (2006.01) | |

(56) References Cited

U.S. PATENT DOCUMENTS

| | | | |
|---|---|---|---|
| 2,884,512 A | 4/1959 | Wakefield | |
| 2,962,582 A | 11/1960 | Croft | |
| 3,252,400 A | 5/1966 | Madl | |
| 3,320,404 A | 5/1967 | Roux | |
| 3,564,794 A * | 2/1971 | Price | E04B 9/32 52/222 |
| 3,655,961 A * | 4/1972 | Hover | E04B 9/02 362/149 |
| 3,774,522 A | 11/1973 | Marsh | |
| 3,780,503 A * | 12/1973 | Smith | B01D 46/12 137/625.31 |
| 4,034,659 A | 7/1977 | Raider | |
| 4,047,336 A * | 9/1977 | Stahlhut | E04B 9/10 52/28 |
| 4,683,699 A | 8/1987 | Larsson | |
| 5,136,486 A | 8/1992 | Burkarth | |
| 5,313,375 A | 5/1994 | Jones | |
| 5,400,553 A * | 3/1995 | Brennan | E04H 3/08 52/106 |
| 5,454,756 A * | 10/1995 | Ludwig | E04B 9/006 454/293 |
| 5,620,369 A | 4/1997 | Spransy | |
| 5,794,397 A * | 8/1998 | Ludwig | E04B 9/006 52/28 |
| 5,865,674 A * | 2/1999 | Starr | B01D 46/0005 454/187 |
| 5,993,311 A * | 11/1999 | Feller | B01D 46/0005 454/187 |
| 6,220,576 B1 | 4/2001 | Chan | |
| 6,351,920 B1 | 3/2002 | Hopkins et al. | |
| 7,513,086 B2 | 4/2009 | Helmus | |
| 1,918,008 A1 | 5/2013 | Kikai et al. | |
| 8,967,832 B2 * | 3/2015 | Zakula | F21V 33/0088 362/294 |
| 9,217,247 B2 | 12/2015 | Behling | |
| 2006/0130658 A1 | 6/2006 | Chang et al. | |
| 2008/0010907 A1 * | 1/2008 | Moench | E04B 9/006 52/28 |
| 2009/0255203 A1 * | 10/2009 | Richardson | E04B 9/06 52/506.06 |
| 2009/0316391 A1 * | 12/2009 | Huang | A47F 3/001 362/133 |
| 2013/0279156 A1 * | 10/2013 | Kaule | F21V 13/04 362/133 |
| 2013/0344795 A1 | 12/2013 | Schreiber | |
| 2014/0160756 A1 * | 6/2014 | Ebner | G09F 13/04 362/244 |
| 2015/0204070 A1 * | 7/2015 | Gierens | F21V 33/006 52/28 |
| 2015/0276169 A1 * | 10/2015 | Bullard | F21V 5/04 362/235 |
| 2016/0273797 A1 | 9/2016 | Bruhnke et al. | |
| 2017/0101779 A1 | 4/2017 | Schreiber | |
| 2017/0334345 A1 * | 11/2017 | Yokoyama | F21S 43/26 |

\* cited by examiner

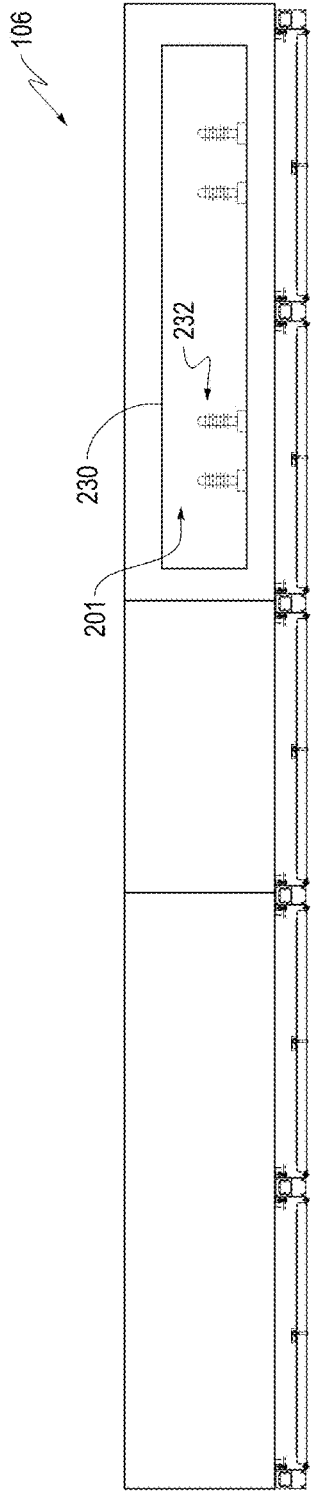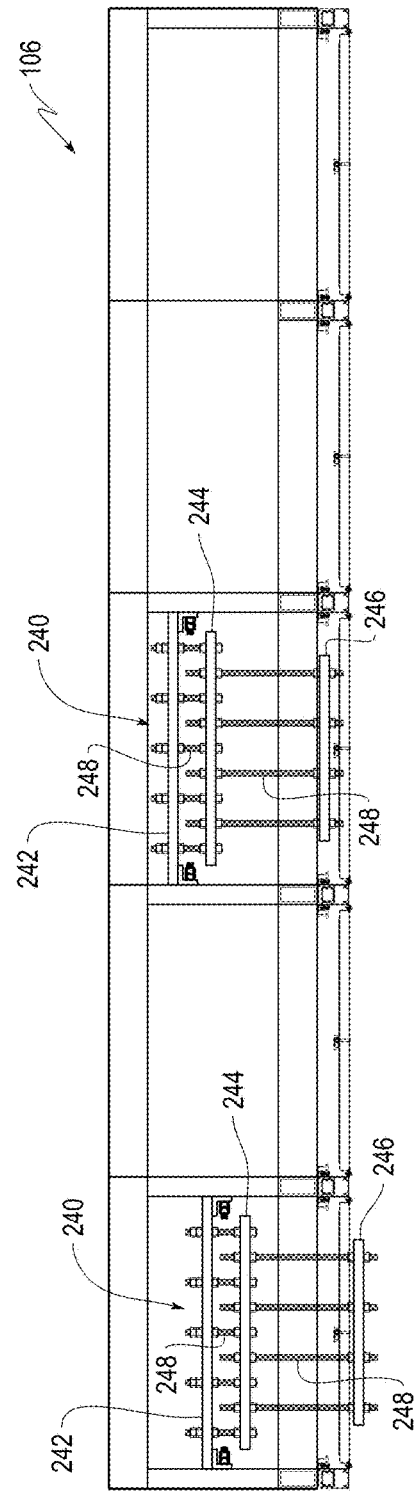
FIG. 4
FIG. 5

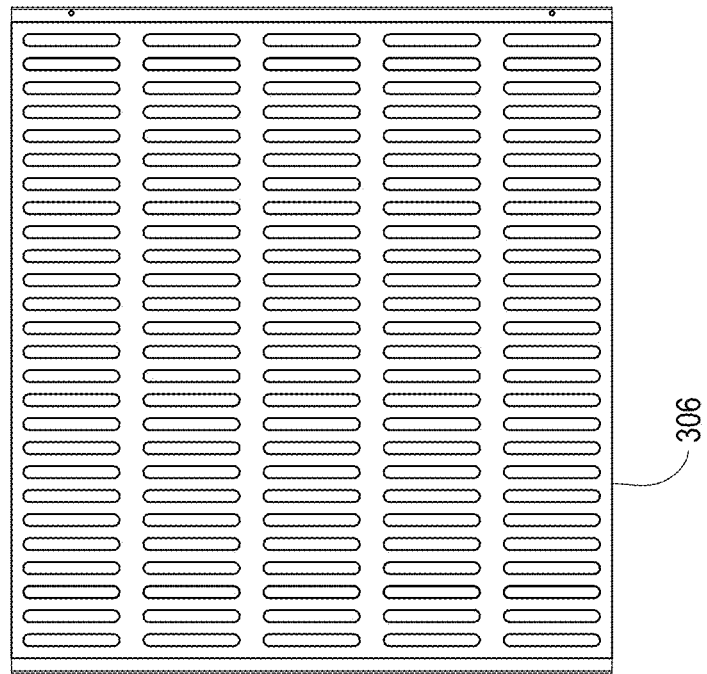
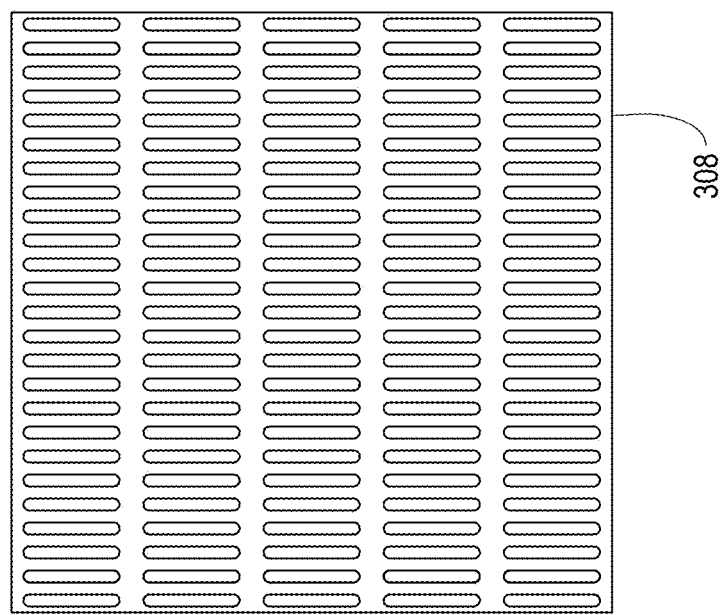
FIG. 17

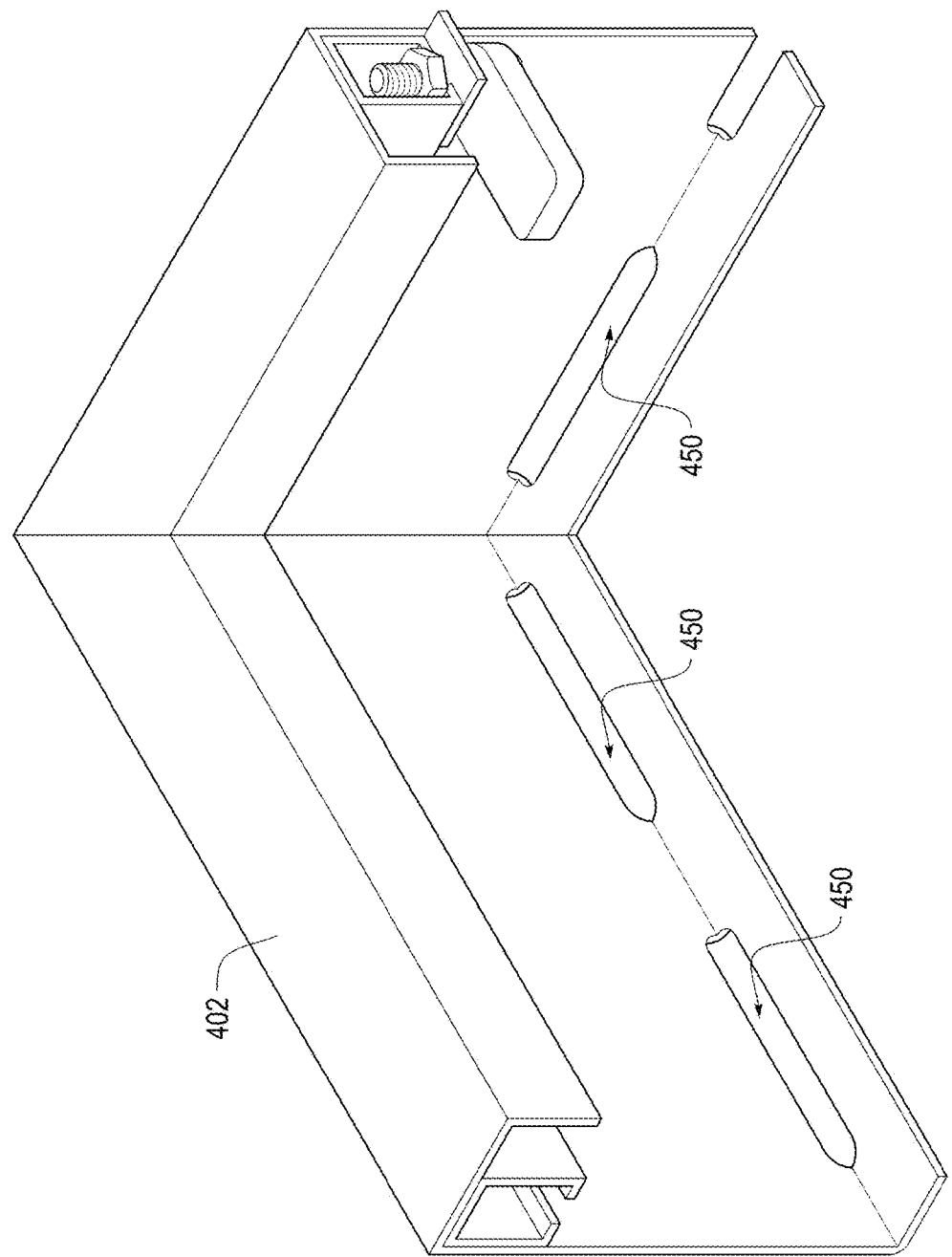

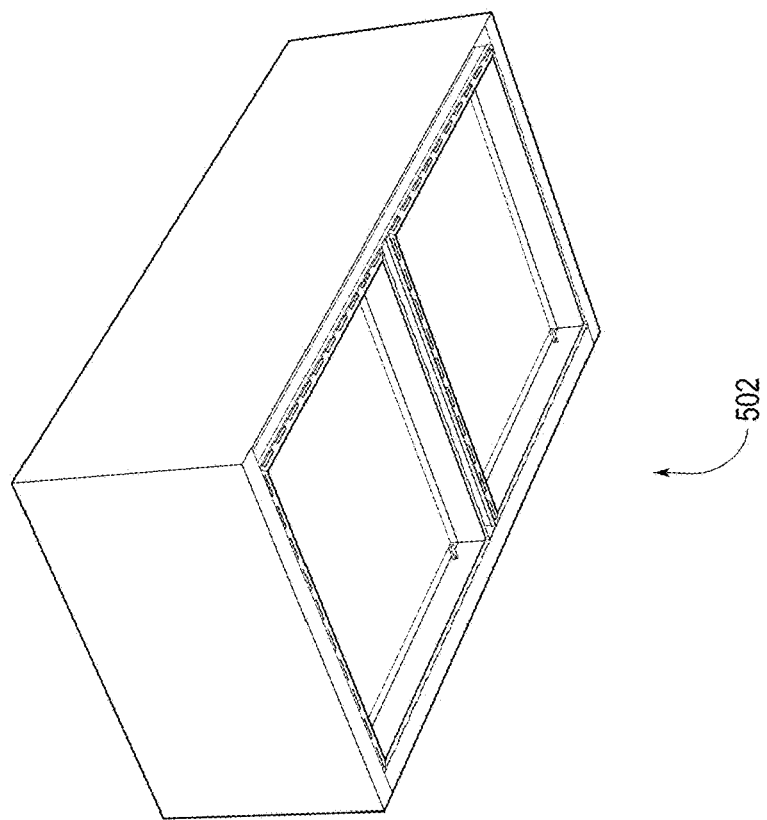
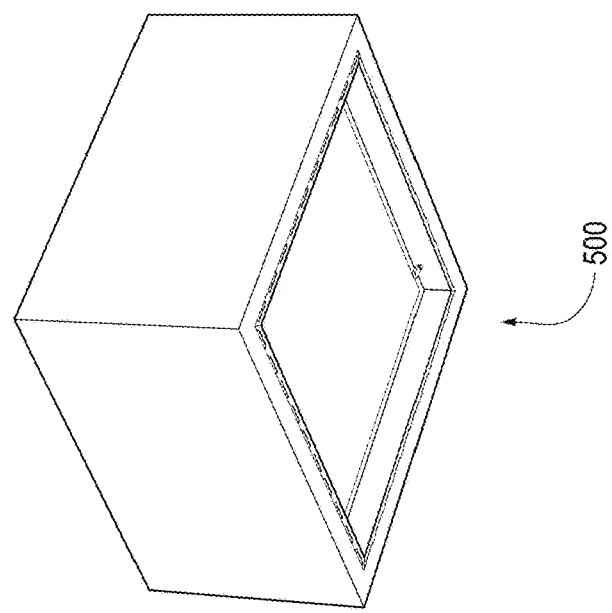
FIG. 22

AIRFRAME SYSTEM AND METHOD OF CONTROLLING AIRFLOW

CROSS-REFERENCE TO RELATED APPLICATIONS

This is a Continuation-in-Part of application Ser. No. 15/288,232, filed Oct. 7, 2016, which claims the benefit of and priority to U.S. Provisional Application No. 62/238,601, filed Oct. 7, 2015. The disclosures of the prior applications are hereby incorporated by reference herein in their entirety.

BACKGROUND OF THE DISCLOSURE

Hospital operating rooms typically include surgical equipment and one or more lights that are located over a surgical site. The surgical equipment may be movable in relation to a surgical site target zone.

Additionally, air supply arrangement may be positioned within a ceiling directly above the surgical light and the surgical site target zone. The air supply arrangement may include vents through which filtered air is supplied and directed toward the surgical site. Sidewall vents return contaminated air from the perimeter of the room to an air filtration system positioned upstream of the supply air array. The air filtration system supplies filtered air to the room through the supply air array with unidirectional, downward airflow.

Because the surgical equipment (e.g., surgical light) may be positioned directly over the surgical target zone, the surgical equipment may block airflow generated by the air supply arrangement and create a low pressure zone underneath the surgical equipment. The low pressure zone causes air turbulence underneath the surgical equipment. Due to turbulent airflow, various contaminants generated through a surgical procedure may be circulated within the surgical environment. For example, surgical staff may carry particulate and bacterial contaminants that may be dispersed directly above a surgical site in the absence of filtered, downward, unidirectional flow. Further, bone fragments, biological fluids, and blood may be projected upward toward the surgical equipment, which is cleaned and sterilized between surgical procedures.

Accordingly, a need exists for a system and method of providing uninterrupted, reduced turbulence airflow within a sterile field and underneath surgical equipment. A need also exists for a system and method that reduces the possibility of contaminants being dispersed over and within a surgical site.

SUMMARY OF THE DISCLOSURE

Certain embodiments of the present disclosure provide an air frame system comprising a frame body defining one or more openings, a plurality of air passages along an inner periphery of the one or more openings, and an airframe grid coupled to the frame body. The airframe grid comprises at least one wireway channel therein. The air frame system further comprises a wireway channel cover clip removably coupled to the at least one wireway channel, a light assembly removably coupled to the airframe grid, and a retainer clip removably coupled to the airframe grid, the retainer clip retaining the light assembly within the airframe grid.

BRIEF DESCRIPTION OF THE DRAWINGS

FIGS. 4 and 5 illustrate lateral internal views of a supply air array, according to an embodiment of the present disclosure.

FIG. 17 is a bottom plan view of a guillotine damper, according to an embodiment of the present disclosure.

FIG. 18 is a top perspective view of an air channel frame showing air passages, according to an embodiment of the present disclosure.

FIG. 22 is a bottom perspective view of light, air-diffusers, according to an embodiment of the present disclosure.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide an airflow system that includes a frame structure that allows for proper airflow within the surgical target zone even when surgical equipment is positioned above the surgical target zone. For example, in various embodiments, low pressure zones that could cause air turbulence underneath the surgical equipment are reduced or eliminated. As such, in various embodiments, because the turbulent airflow is reduced or eliminated, various contaminants generated through a surgical procedure are not circulated within the surgical environment.

One or more embodiments provide an airframe structure that is configured to channel air, which may be filtered, sterilized or purified, to the surgical target zone with minimal or no air turbulence underneath the surgical equipment. Various embodiments provide an integrated and modular arrangement to effectively deliver airflow directly to the surgical target zone.

Figure 1:
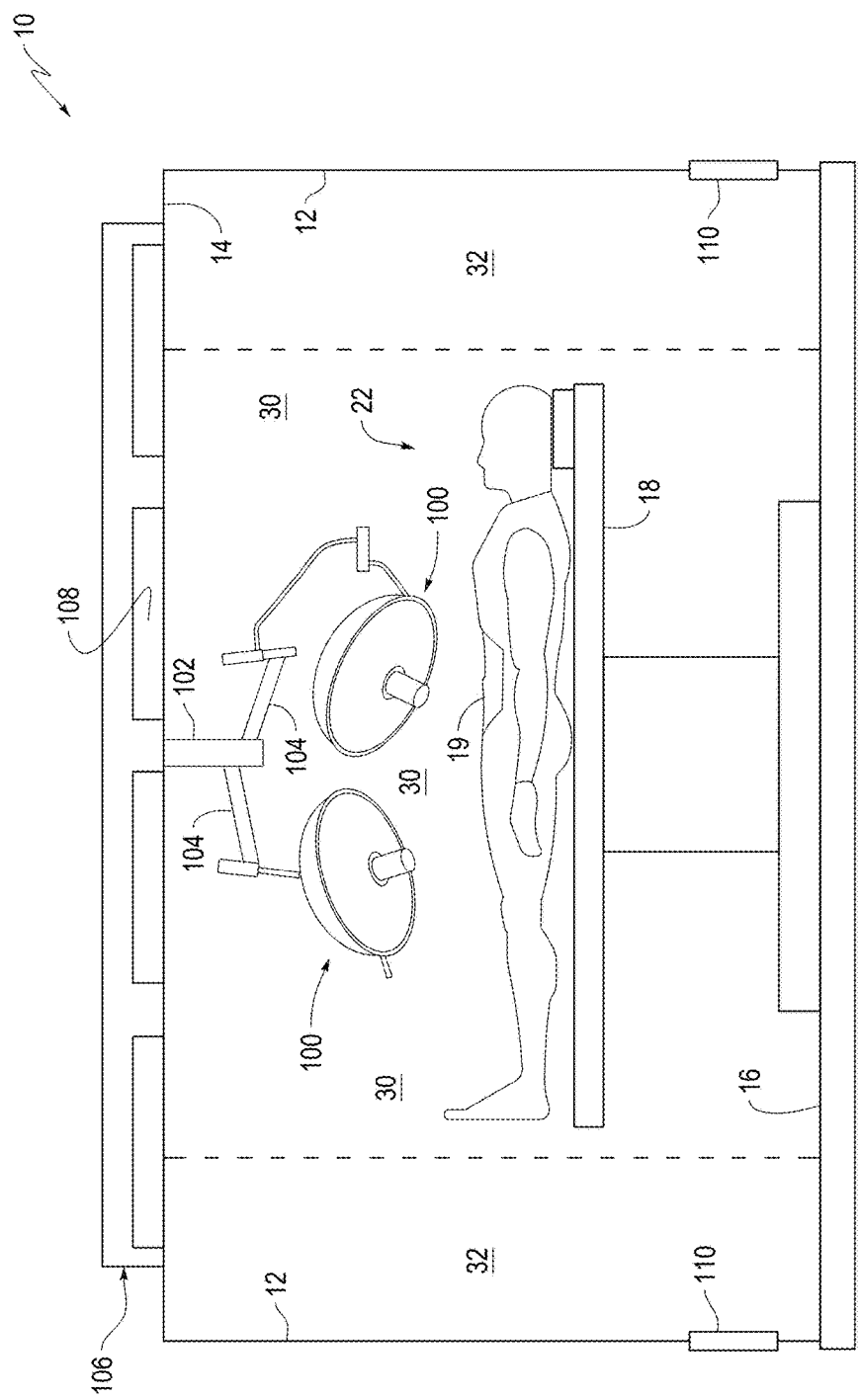
FIG. 1 illustrates a lateral view of an operating room, according to an embodiment of the present disclosure.

FIG. 1 illustrates a lateral view of an operating room 10, according to an embodiment of the present disclosure. The operating room 10 may be defined by walls 12, a ceiling 14, and a floor 16. An operating table 18 may be supported on the floor 16. The operating table 18 may include a support bed 20 that is configured to support a patient 22. A surgical site 19 may be located on the patient 22.

Surgical equipment, which in the illustrated embodiment is a surgical light system 100 is suspended from the ceiling 14 above the operating table 18, which may define a sterile field 30. A support beam 102 extends downwardly from the ceiling 14. One or more boom arms 104 may extend from the support beam 102. As shown in FIG. 1, two surgical light assemblies 100 may be coupled to two separate and distinct boom arms 104. Alternatively, more or less surgical light assemblies 100 than shown may be used. It should be appreciated that surgical light system 100 is shown only for illustrative purpose and different or additional surgical equipment may be suspended from the ceiling 14.

A supply air array 106 (also referred to as an air frame system) is secured to the ceiling 104. The supply air array 106 is configured to direct airflow into the operating room 10 and in various embodiments defines a supply air frame. The supply air array 106 may include one or more air diffusers 108 (or air delivery modules). Additionally, one or more return vents 110, which may be secured to one or more walls 12 are provided. In the illustrated embodiment, the supply air array 106 directs airflow into the operating room through the diffusers 108. The airflow passes into the return vents 110, which channel the airflow back into the supply air array 106, where the airflow is filtered and directed back into the operating room through the air diffusers 108. As discussed in more detail herein, the supply air array 106 is configured to control airflow in operating room 10 such that air is directed from the sterile field 30 to a non-sterile field 32 without being recirculated back into the sterile field 30. Thus, airflow is directed from the supply air array 106 into the sterile field 30 then to the non-sterile field 32 and finally into the one or more return vents 110.

The supply air array 106 is also configured to include an integrated lighting structure that includes a plurality of light sources as described in more detail herein. Accordingly, in various embodiments the supply air array 106 defines an integrated unit that may be installed with electrical components and air supplies connected to a single structural element. Thus, a laminar airflow is created directly to the surgical target zone that creates an airflow pressure to reduce or prevent turbulence, which is also being lit by the integrated lighting.

Figure 2:
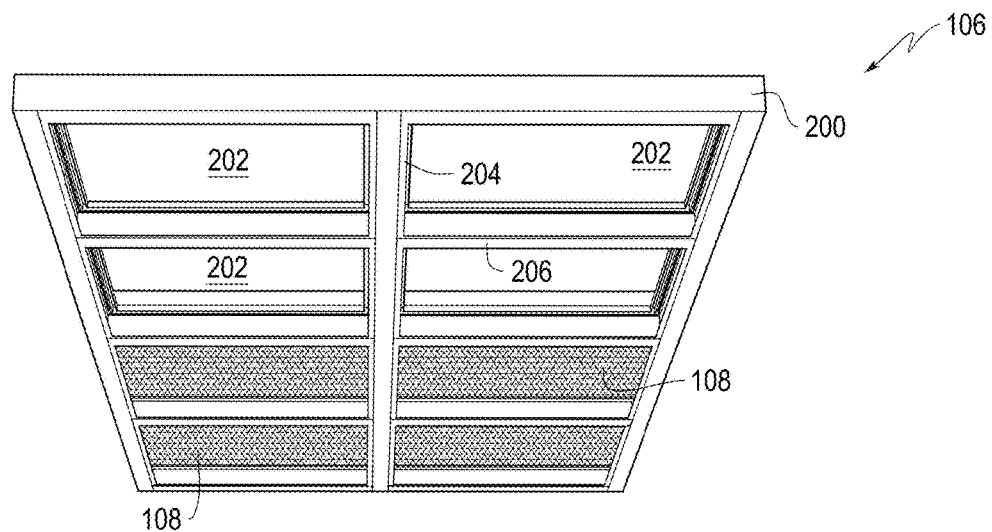
FIGS. 2 and 3 illustrate perspective bottom views of a supply air array, according embodiments of the present disclosure.

FIG. 2 illustrates a perspective bottom view of the supply air array 106, according to an embodiment of the present disclosure. The supply air array 106 in the illustrated embodiment includes a lower frame 200 having a plurality of openings 202 defined therein by cross-members 204 and 206. It should be noted that although the illustrated embodiment shows a 2 cell×4 cell array, the supply air array 106 may be sized differently, including having a single opening 202. Additionally, the openings 202 may be sized and shaped differently than illustrated, for example, based on design requirements or constraints. In the embodiment shown in FIG. 2, the front four openings 202 are illustrated with nothing therein and the back four opening 202 illustrate air diffusers 108 coupled within the openings 202. As can be seen, the air diffusers 108 are coupled with the openings 202 such that the air diffusers 108 are recessed within the openings 202 in this embodiment.

Figure 3:
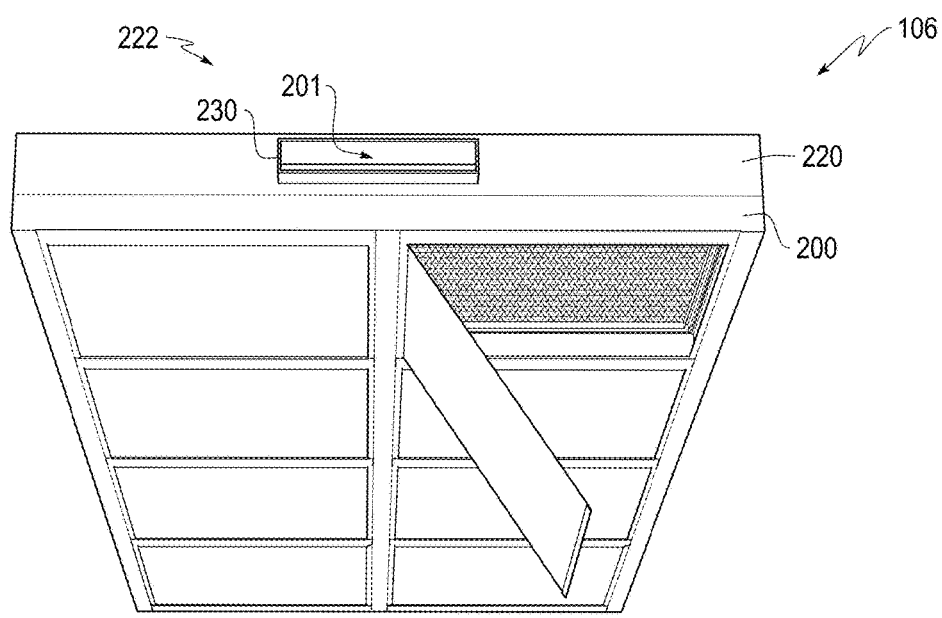

FIG. 3 illustrates a perspective bottom view of the supply air array 106 in which all of the openings have air diffusers 108 coupled therein and shows that the air diffusers 108 may be hingedly mounted to one side of the openings 202 such that access may be provided within the openings 202, as well as to both sides of the air diffusers 108 (e.g., to clean the air diffusers 108 or to install HEPA filters). As can be seen in FIG. 4, a top cover 220 is coupled above the lower frame 200 (e.g., by an airtight seal) to define a pressure air space above the lower frame 200. In the illustrated embodiment, an air coupler 222 is provided on one end of the top cover 220 to allow coupling to an air supply that provides airflow into the top cover 220. The air coupler is made up of a supply air passage 201 and a supply air connection flange 230. There may be more than one air coupler 222 which may be positioned at any location on the top, the sides or the ends of the top cover 220. In operation, air supplied into the top cover 220 is directed into the sterile field 30 (shown in FIG. 1) to define a non-turbulent laminar flow.

Figure 6:
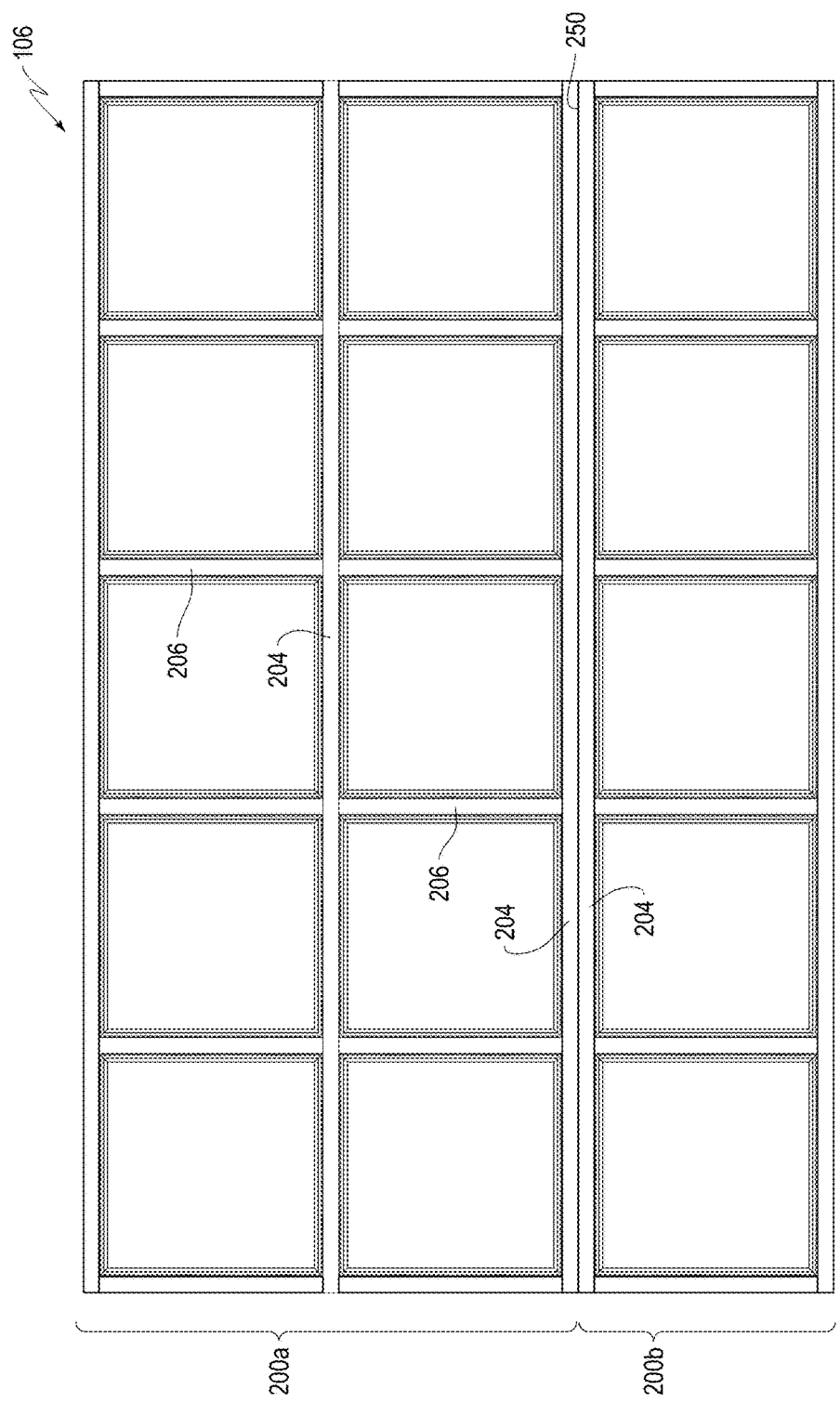
FIG. 6 illustrates a bottom plan view of a supply air array, according to an embodiment of the present disclosure.

FIGS. 4 and 5 are elevation views of the supply air array 106 and FIG. 6 is a bottom plan view of the supply air array 106. In the illustrated embodiment, an air supply connection 230 may be provided that includes a cleansing system, shown as a sterilization system 232. As discussed herein, the cleansing system may include an air filtering system, the sterilization system 232 and/or an air purifying system. The cleansing system may be placed at any location within the supply air array 106 or upstream of the supply air array 106. The cleansing system is positioned up stream of the opening 202 such that air that passes through the opening 202 is cleansed.

The supply air array 106 includes an adjustable mounting arrangement 240 that allows for varying the height of components, such as the boom arm 102 mounted within the openings. In particular, the adjustable mounting arrangement 240 defines mounting locations within the each opening 202 of the lower frame 200. The adjustable mounting arrangement 240 in the illustrated embodiment includes a mounting plate 242 that may be mounted within the opening 202 at different locations, in particular, different vertical locations within the opening 202. For example, predefined mounting locations (e.g., mounting bores) may be located on opposing walls of the opening 202 for coupling thereto of the mounting plate 242 (e.g., bolt mounting of the mounting plate 242 to walls of the opening 202). The predefined mounting locations provide a coarse mounting arrangement within the opening 202. For example, as can be seen in FIG. 5, the two mounting plates 242 are mounted at different vertical heights within respective openings 202.

The mounting plates 242 couple to a secondary plate 244 that allows for adjustable mounting thereto of a bottom plate 246. For example, plural bolts 248 may couple the secondary plate 244 (or intermediate plate) to the bottom plate 244 to allow finer height adjustment within the opening 202. As can be seen in FIG. 5, the bottom plate 244 in the different openings 202 extend a different distance from the secondary plate 244 such that the bottom plate 244 in each of the openings 202 is positioned at different vertical heights. As should be appreciated, components to be mounted within each of the openings 202 may be mounted at the same or different vertical heights.

As shown in FIG. 6, the cross-members 204 and 206 define an airtight arrangement wherein airflow is directed around the cross-members 204 and 206 into the openings 202, which will be described in more detail herein. Additionally, separate lower frames 200 may be coupled together at a seam 250. For example, in the illustrated embodiment, a lower frame 200a defining a 2 cell×5 cell supply air array 106 is coupled with a lower frame 200b defining a 1 cell×5 cell supply air array 106. The lower frames 200a and 200b may be coupled together using any suitable fastening arrangement, such as coupling together by bolts.

Figure 7:
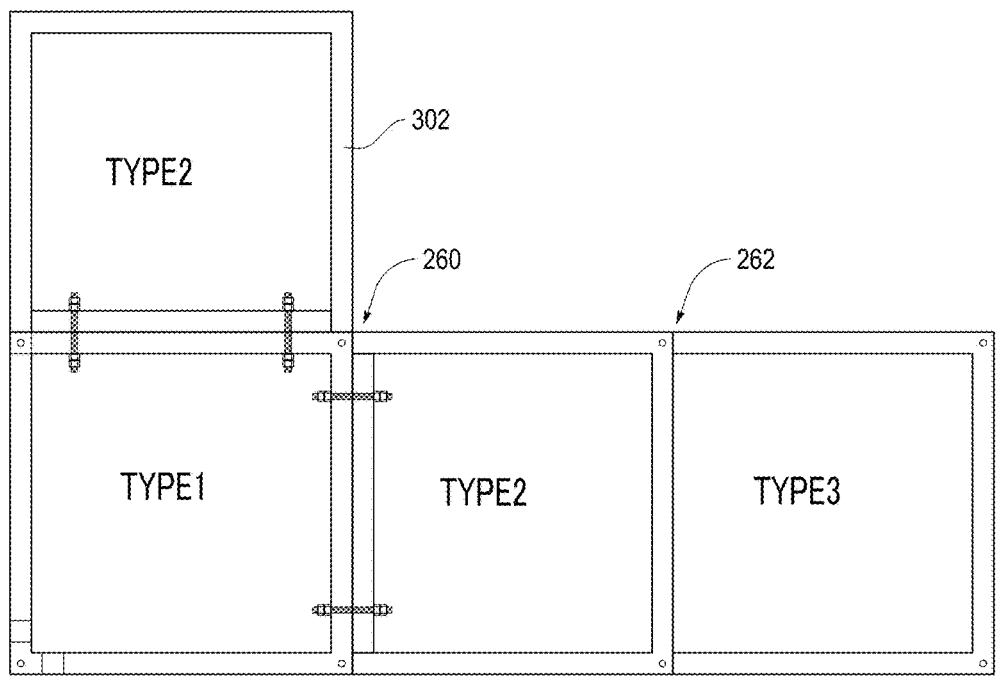
FIG. 7 illustrates a bottom plan view of modular units coupled together, according to an embodiment of the present disclosure.
Figure 8:
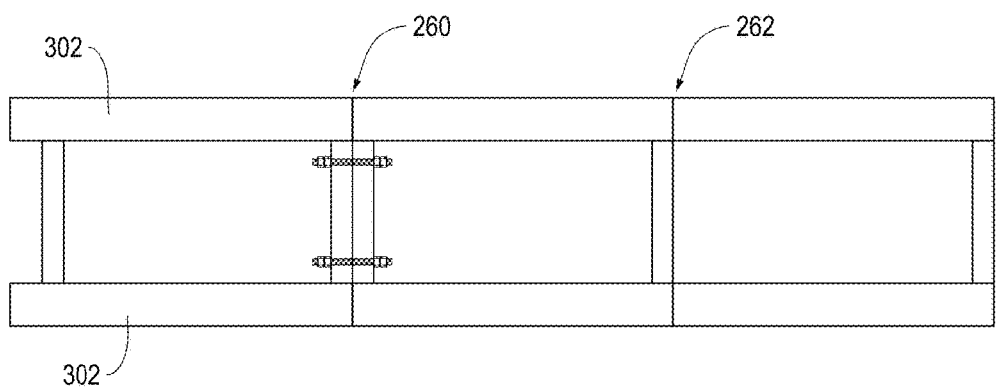
FIG. 8 illustrates a side elevation view of modular units coupled together, according to an embodiment of the present disclosure.

As illustrated in FIGS. 7 and 8, different modular elements (shown as three different types of modular units) defining the openings 202 in the supply air array 106 may be coupled together with a bolted connection 260 or a welded connection 262. Thus, different sized and shaped supply air arrays 106 may be provided that include different types of modular elements. The different types of modular elements may include different elements, such as the diffusers 108, lights or other components that would be desirable or needed in the operating room 10. In some embodiments, the supply air array 106 may include the lower frame 200 with components, a light housing with components, a wireway with components and/or a hinged screen and airflow control damper (such as the airflow dampers 108). In various embodiments, plural air diffusers 108 are installed with the top cover 220 having a top or side mounted air duct collar.

Figure 9:
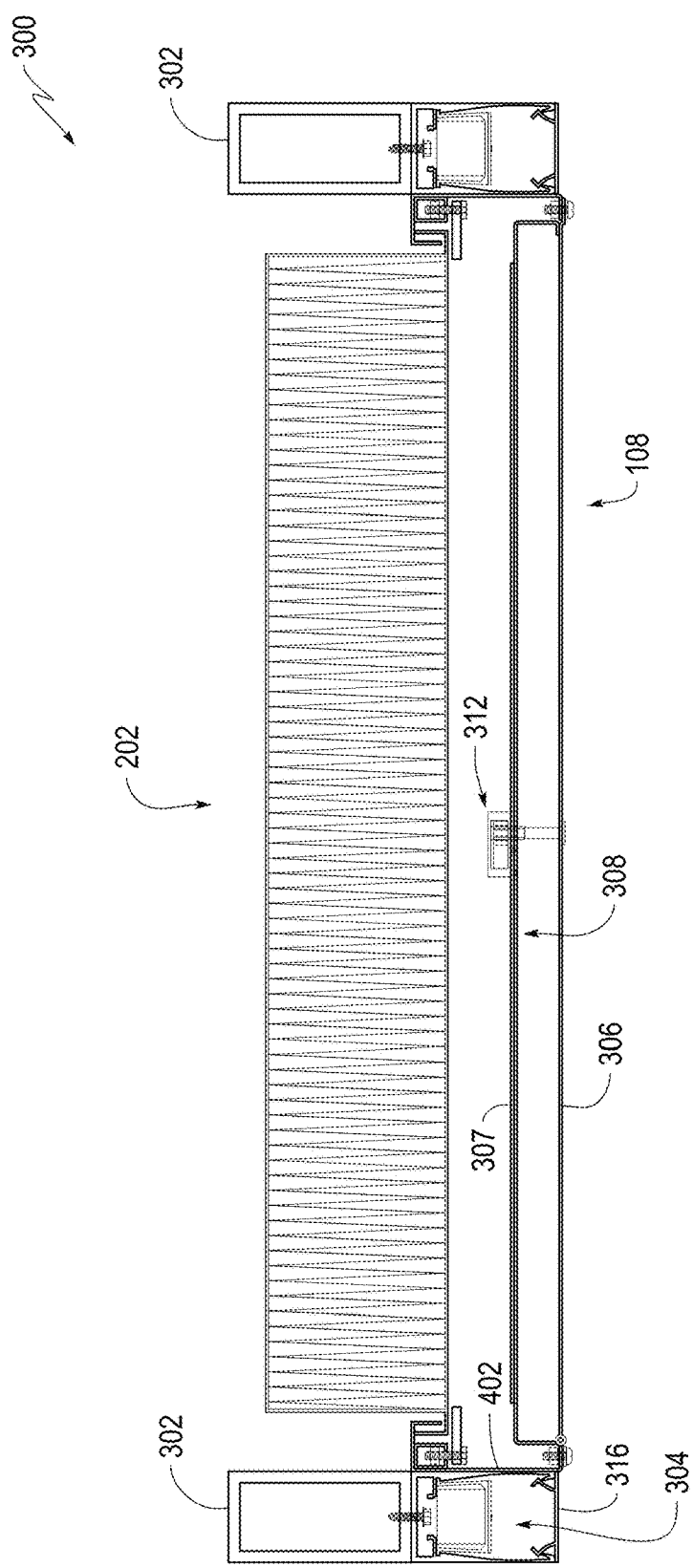
FIGS. 9 and 10 illustrate side elevation views of a portion of a supply air array showing a diffuser screen, damper and filter arrangement, according to an embodiment of the present disclosure.

FIG. 9 illustrates a single modular element 300, according to an embodiment of the disclosure. The modular element 300 is defined by the opening 202 between supporting members, which in this embodiment are hollow structural section (HSS) tube frames 302 that may be mounted, for example, to a truss system, such as described in co-pending patent application Ser. No. 15/288,168 entitled Equipment Support System and Method of Supporting Equipment in a Surgical Environment, filed on Oct. 7, 2016, or to the ceiling 14. The HSS tube frames 302 may include a snap-fit light assembly 304 coupled to the HSS tube frames 302 (illustrated as coupled with a bolt). The light assembly 304 may be a suitable light source for an operating room environment and include a light lens 316 at a bottom surface thereof.

In the embodiment of FIG. 9, the air diffuser 108 includes a screen 306 and a damper 308 (also shown in FIG. 17) that extend across the opening 202, which may be adjusted (e.g., rotated) by a tool, such as an Allen wrench, causing the damper 308 to open or close (in a guillotine type configuration). The screen 306 and damper 308 are coupled together as a single unit and hingedly coupled to one end of the opening 202, for example, to a lower end of an airframe channel 402 in which the light assembly 304 is coupled. The damper top plate 307 and damper 308 arrangement includes a damper adjustment mechanism 312 that allows for movement of the damper top plate 307 and damper 308 relative to each other to adjust airflow therethrough. Thus, an airflow control damper may be defined.

Figure 10:
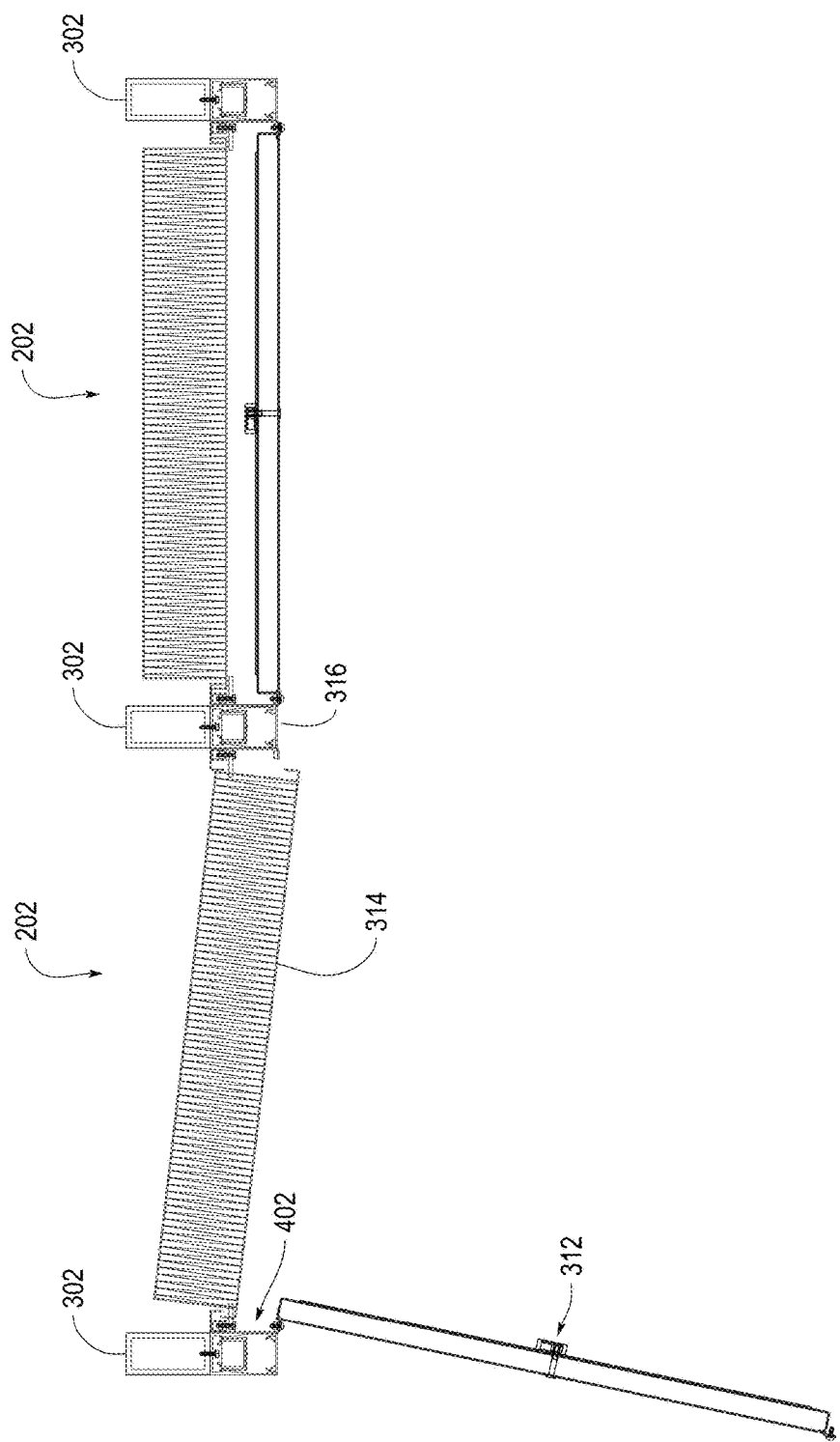
Figure 12:
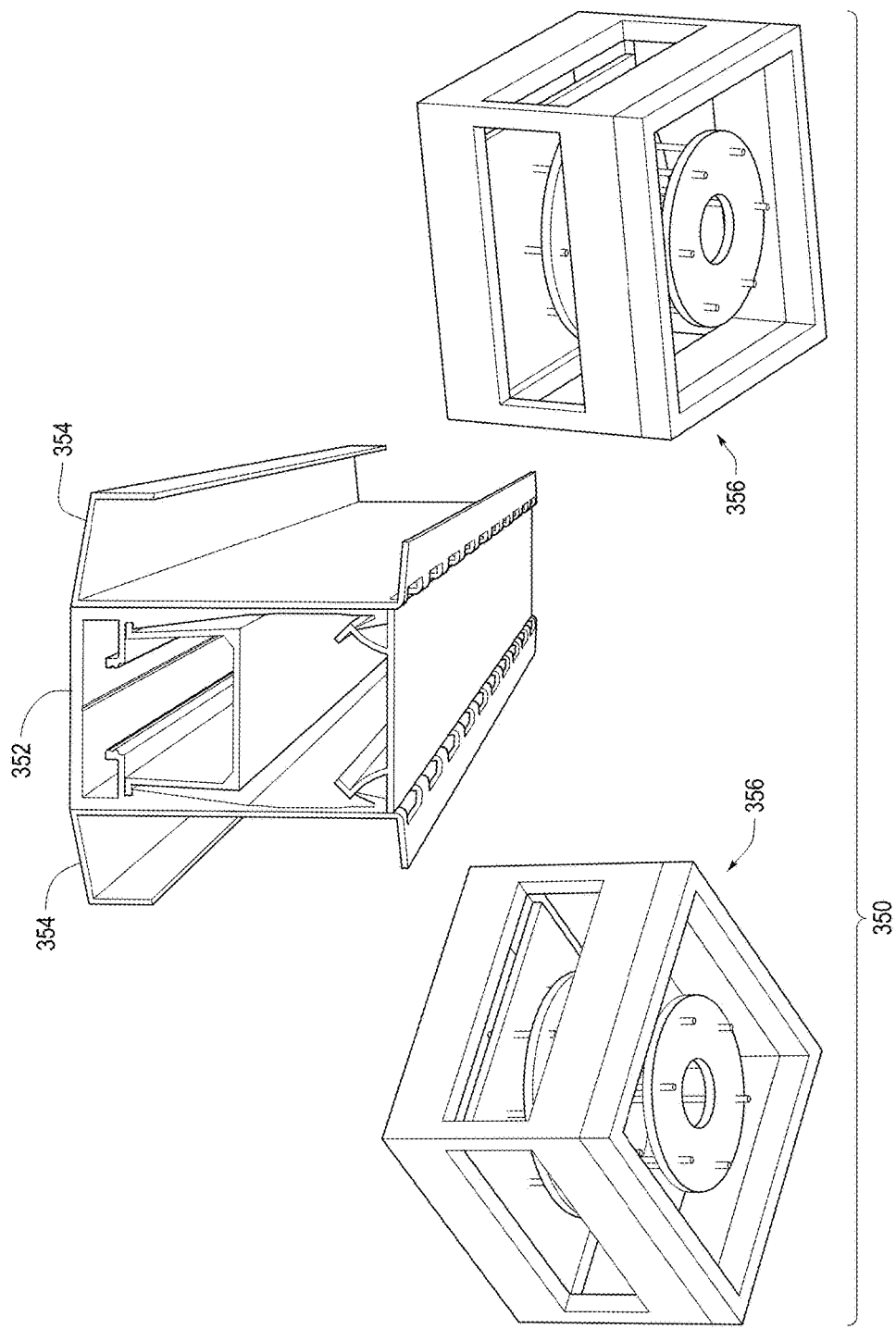
FIG. 12 illustrates an assembly and structural mounts, according to an embodiment of the present disclosure.

As can be seen in FIG. 10, an air cleansing member, illustrated as an air filter 314, such as a high-efficiency particulate arrestance (HEPA) filter may be provided. The air filter 314 is removably coupled within the opening 202 to allow for removal and replacement within the opening 202. For example, a knife edge seal and HEPA lock may be provided as illustrated in FIG. 12.

Figure 11:
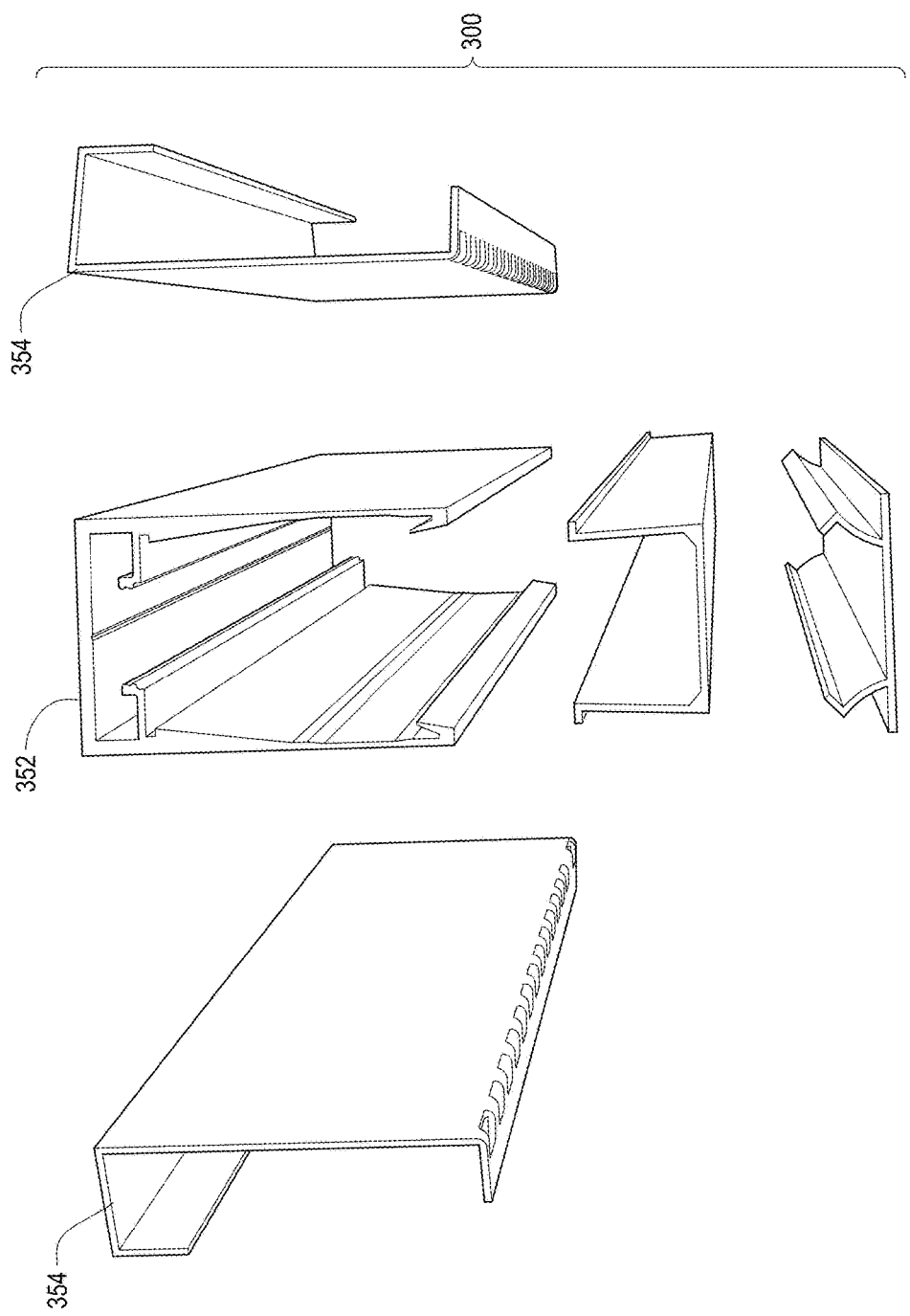
FIG. 11 illustrates a perspective view of components, according to an embodiment of the present disclosure.

Various embodiments, thus, provide air delivery and lighting in a modular, easily to install configuration. In various embodiments, an airframe system 350 may be provided, components of which are shown in FIG. 11. The components may be coupled together in different configurations as desired or needed, and as discussed herein. FIG. 11 illustrates base components in accordance with some embodiments. Illustrated in FIG. 11 are portions of various components, the components include a portion of a lighting module 352 (shown in an exploded view, the elements of which couple together without fasteners) and portions of air delivery modules 352, which may be sized and shaped based on a particular configuration. In various embodiments, the modules define separate systems or sub-systems to deliver the different features, including lighting and air. As illustrated in FIG. 12, the lighting module 352 is coupled to air delivery modules 352 (to define a lighting and air delivery sub-system) that is integrated with one or more structural mounts 356, such as by mounting these components together in a desired arrangement or configuration. It should be noted that in various embodiments, there is no penetration into the light cavity (e.g., inside the lighting module 352) as a result of the rivet holes for mounting being located in the airframe.

With reference now to FIGS. 13-16, various elements of the structural support for the supply air array 106 will now be described. In particular, the HSS tube frame 302 may be coupled with a light housing 400 (which may be embodied as the lighting module 352) having upper engagement members 304 and lower engagement member 404 that provide a snap fit coupling with the light assembly 304 and the lens 316, respectively (without the need for hardware fasteners). Additionally, the light housing 400 may be coupled with airframe support members 402 (which may be embodied as the air delivery modules 354) that are mounted to a support structure, such as the wall 12 or ceiling 14 of the operating room 10. The light housing 400 with the airframe support members 402 together define air frame channels of the supply air array 106. Variations and modifications are contemplated. For example, in some embodiments, a thumb tab release is provided in combination with a retainer clip 305 within the light housing 400 for easier removal of the components within the light housing 400.

Figure 13:
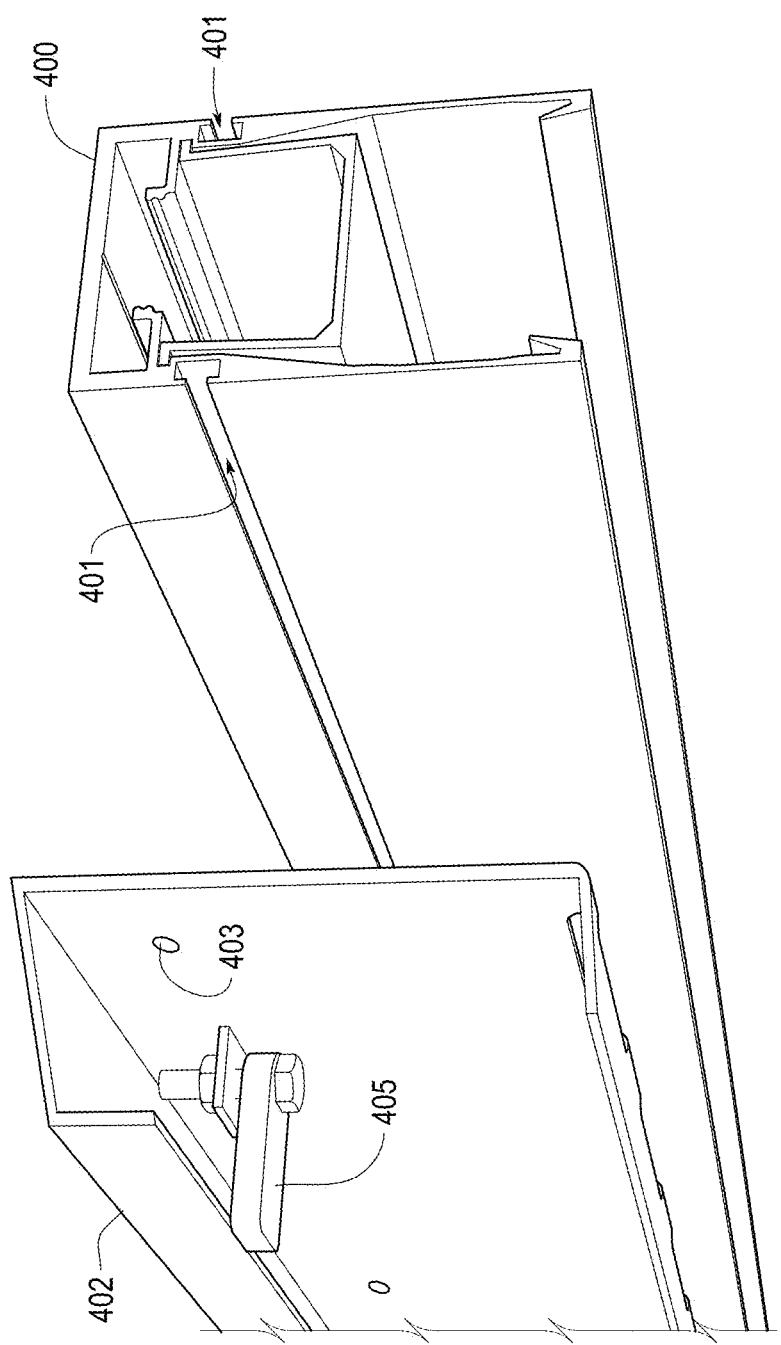
FIG. 13 illustrates a coupling arrangement, according to an embodiment of the present disclosure.
Figure 14:
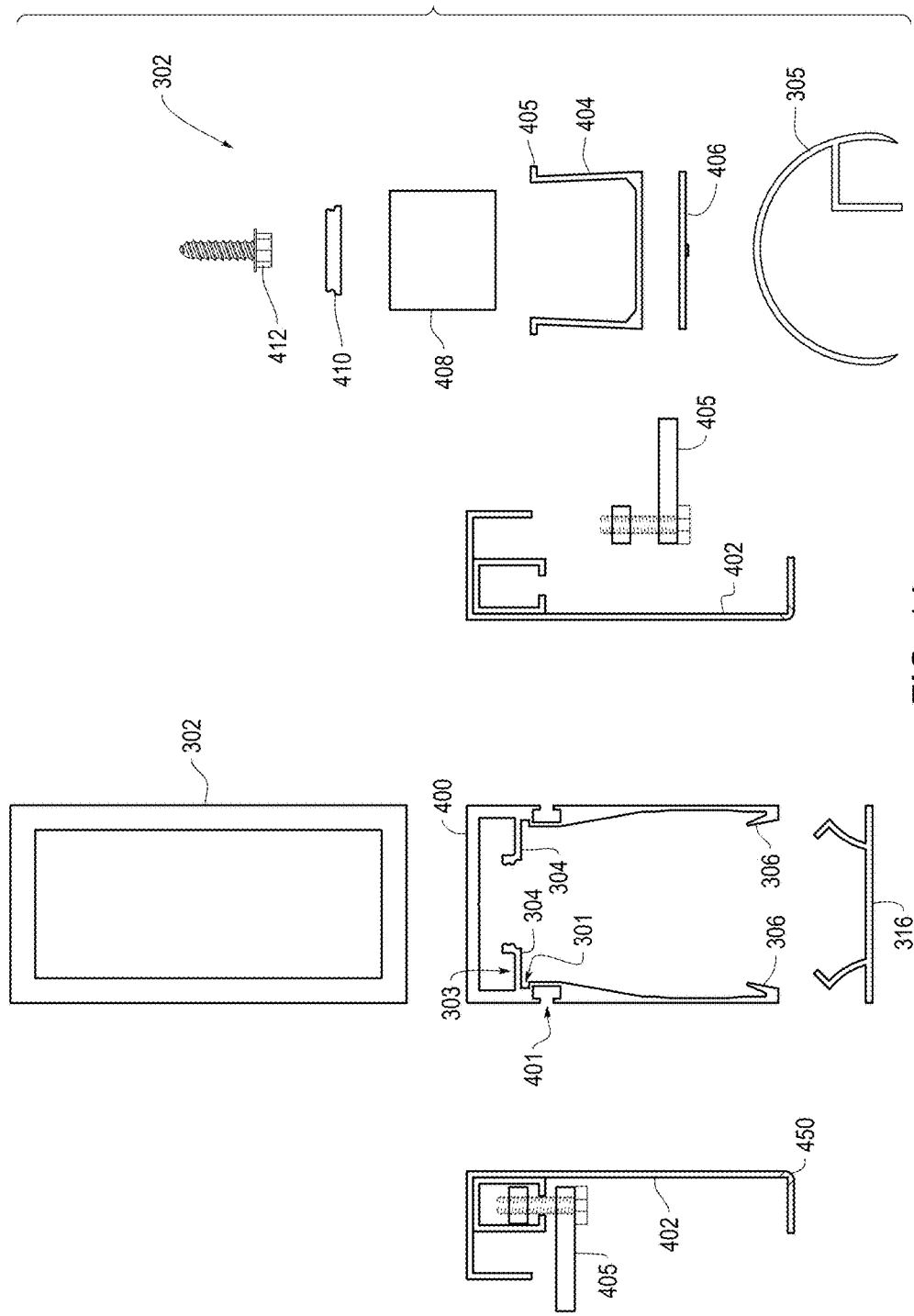
FIG. 14 is an exploded view of a light and air frame arrangement, according to an embodiment of the present disclosure.
Figure 15:
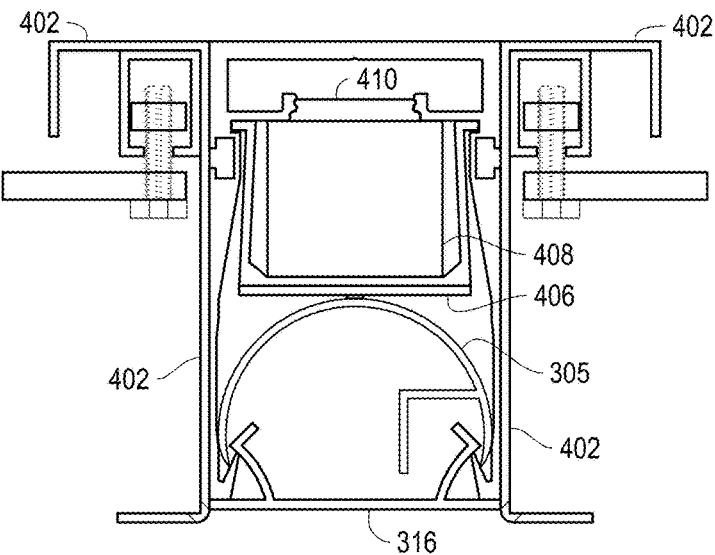
FIGS. 15 and 16 are side elevation views of assembled light and air frame assemblies, according to an embodiment of the present disclosure.
Figure 16:
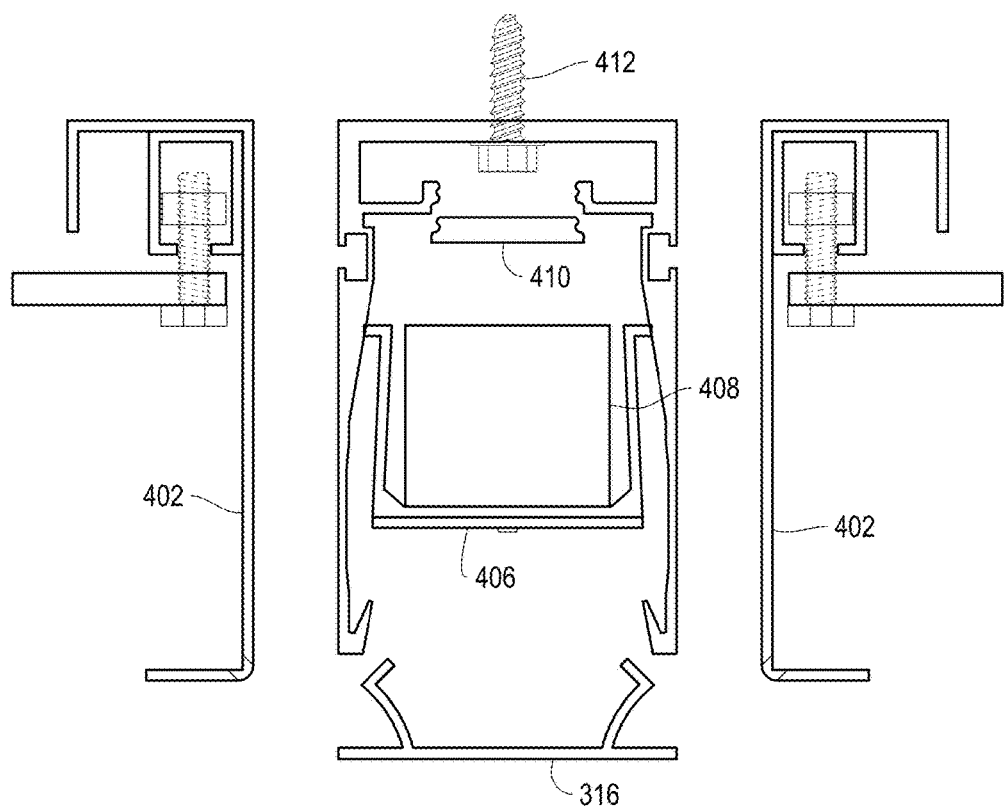

For example, as shown in FIG. 13, the light housing 400, which is illustrated as a light bar, includes mounting tracks, illustrated as rivet tracks 401 (illustrated as grooves extending longitudinally along the outer walls of the light housing 400) to which the airframe 402 is coupled by a rivet 403. As should be appreciated, the rivet tracks 401 allow the airframe 402 at any suitable location along the light housing 400. A HEPA lock 405 may be provided on the airframe 402 (illustrated as a locking arm coupled within the airframe 402) that allows for releasably securing a HEPA filter (or other filtering device) within the airframe 402 as discussed in more detail herein.

With respect to the light assembly 304 that is coupled within the light housing 400, a control housing 404 is coupled to an LED board 406 (light source) and is configured to receive therein a light controller 408. A wireway plug 410 is coupled to the bottom of a wireway cavity 303. A bolt 412 couples the light housing 400 to the HSS tube frame 302. The control housing 404 is configured with male protrusions 405 for snap fit engagement with an upper female cavity 301. In particular, the width of the light housing 400 narrows from bottom to top (as viewed in the Figures) such that control housing 404 is compressed and snap fit therein engaging the male protrusions 405 into the female cavity 301.

Figure 20:
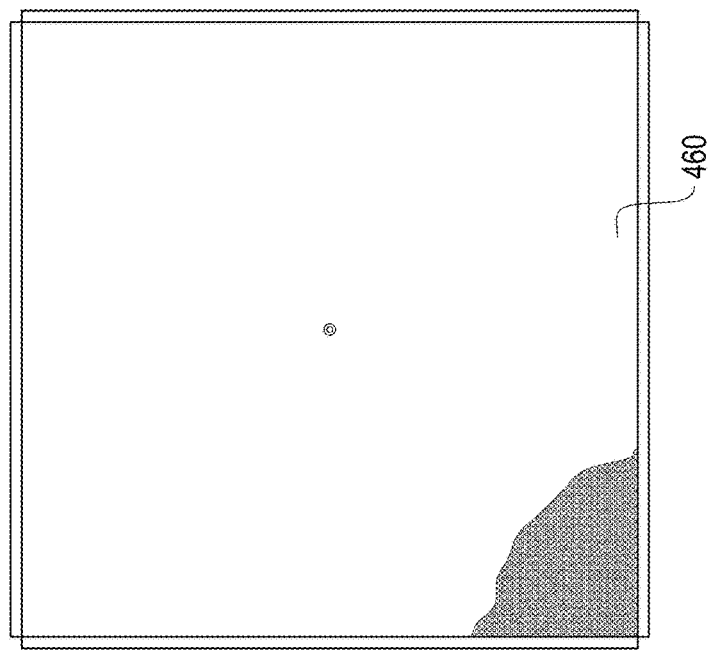
FIG. 20 is a bottom plan view of a diffuser screen, according to an embodiment of the present disclosure.
Figure 19:
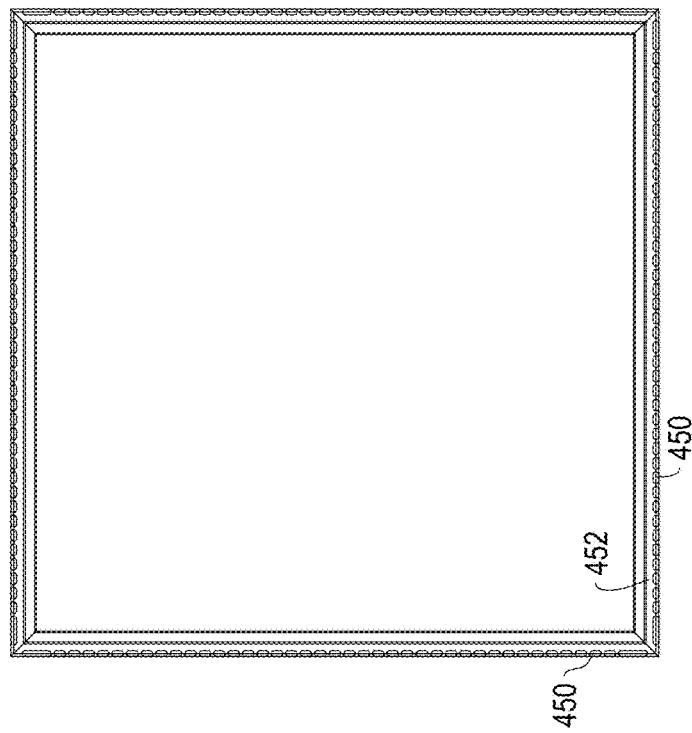
FIG. 19 is a bottom plan view of an air channel frame showing air passages, according to an embodiment of the present disclosure.
Figure 21:
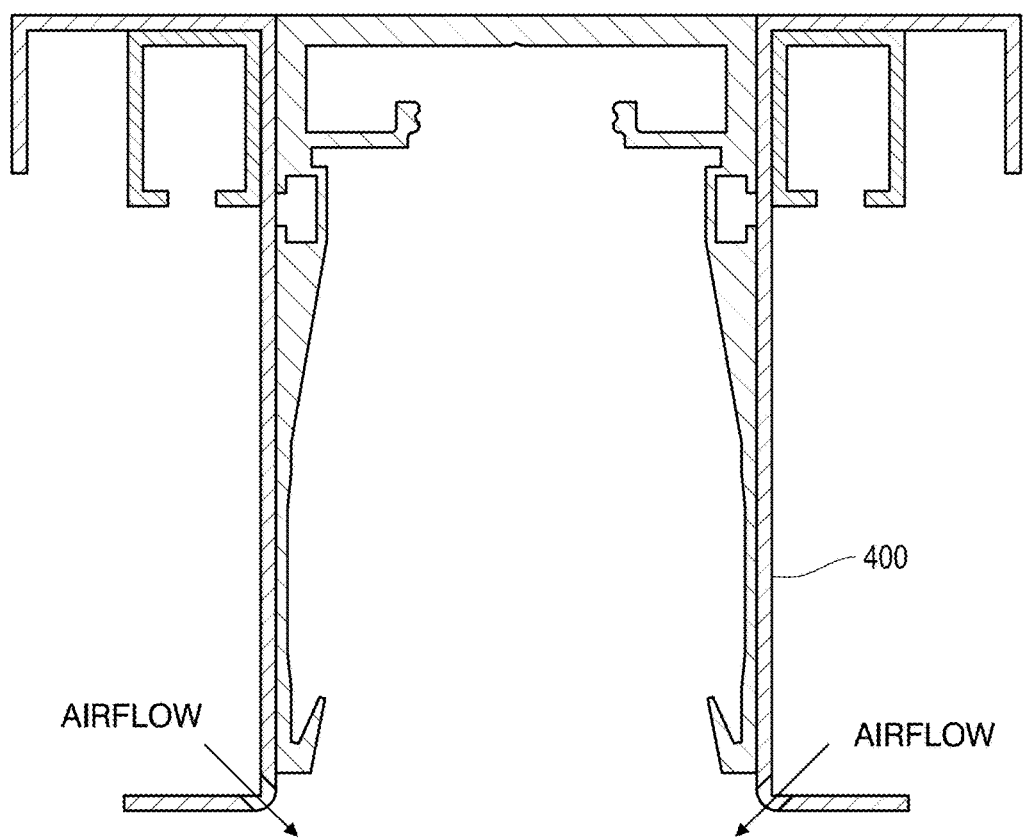
FIG. 21 is a side elevation view of a light assembly and air channel frame showing airflow, according to an embodiment of the present disclosure.

With reference now to FIGS. 18 and 19, the supply air array 106 includes the lower frame 200 that defines an air frame 402 with plural air passages 450 (airflow openings) along an inner edge 452 of each of the openings 202. For example, plural spaced apart openings 450 formed around the periphery of the opening 202 define airflow outlets. The plural air passages 450 allow airflow therethrough, which is directed at an angle downward, for example, by the size, shape and orientation of the air passages 450. Thus, the air passages 450 are configured to direct airflow at an angle downward underneath the light housing 400. For example, an airflow outlet through the plural air passages 450 may be formed within the airframe directly adjacent to the periphery of a diffuser screen 460 as shown in FIG. 20 to direct airflow as shown by the arrows AF in FIG. 21. The airflow directed through the air passages 450 creates a pressure zone underneath the light housing 400 allowing for consistent pressure and airflow beneath the entire supply air array 106.

In some embodiments, a light diffuser structure may be formed in accordance with disclosure herein. For example, FIG. 22 illustrates a 2×2 light diffuser 500 and a 2×4 light diffuser 502. However, as should be appreciated, different sized configurations of light diffuser may be provided.

Figure 23:
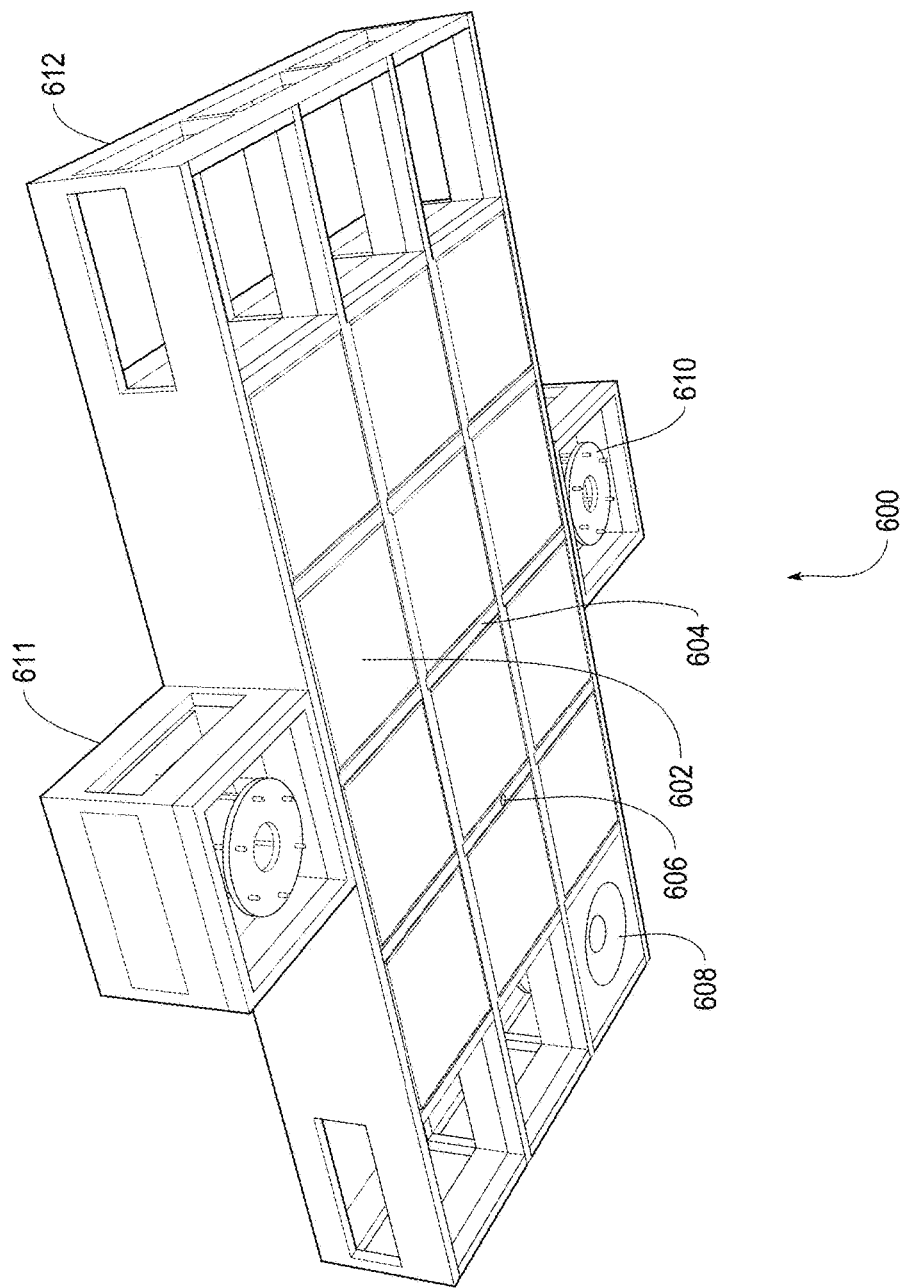
FIG. 23 is a perspective view of an integrated system with modules, according to an embodiment of the present disclosure.

Thus, various embodiments provide an air frame structure that can include lighting, wherein an air conduit is provided within the air frame structure to direct air into the sterile field 30. The various embodiments allow for the integration of multiple components into an easy to install and customizable system 600, such as shown in FIG. 23. The components may be formed or defined by modules or sub-systems that are coupled together as described herein. In the illustrated embodiment, the system 600 can include one or more air delivery modules 602, one or more lighting modules 604 (illustrated as LED lighting modules), one or more fire suppression modules 606, one or more audio/video modules 608 and one or more structural mounts 610, as described in more detail herein. Structural mounts may be configured as a single cell, Flex mount 610 or as a multiple cell arrangement 612. In the various embodiments, with a pressurized module (which may be embodied as or form part of the top cover 220 (shown in FIG. 3) that allows for simple and easy air source hook-up (e.g., contractor hook up, such as a single or dual S/A connection) and having improved quality and performance. The system 600, thus, provides single point air source connection instead of multiple connection points, resulting in less potential for air loss, less sealing and lower complexity. The system 600 also provides high performance controlled airflow, which includes controlling contaminants (that can be beneficial, such as to protect a patient in an operating room having the system 600 installed), using the plurality of modules as described herein.

It should be noted that in the system 600, the structural mounts 610 may be located (e.g., mounted) along the perimeter of the system 600, thereby being located along the perimeter of the airfield. In this configuration, air flow within the airfield is improved by not having the mounts within the portion of the system 600 that includes the airfield. It should also be noted that field connections can be made prior to equipment installation, thereby providing improved access for services, such as for power, data, audio/video, lighting and communications, among others. In some embodiments, one or more of the modules may include interface of connectors, such as a MedGas manifold with field piping performed prior to equipment installation.

Figure 24:
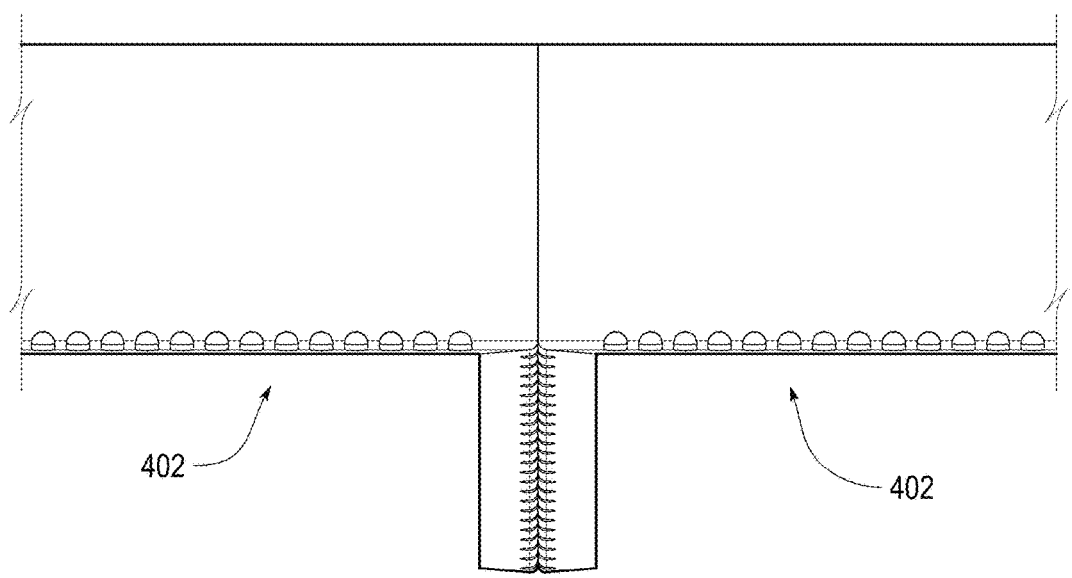
FIG. 24 is a plan view of portions of airframes, according to an embodiment of the present disclosure.

Various embodiments also allow single trade, single source responsibility of the system, instead of multiple trade, multiple source responsibility. In various embodiments, the airframe members 402, such as of adjacent modules, are mounted in abutting engagement as shown in FIG. 24.

Figure 25:
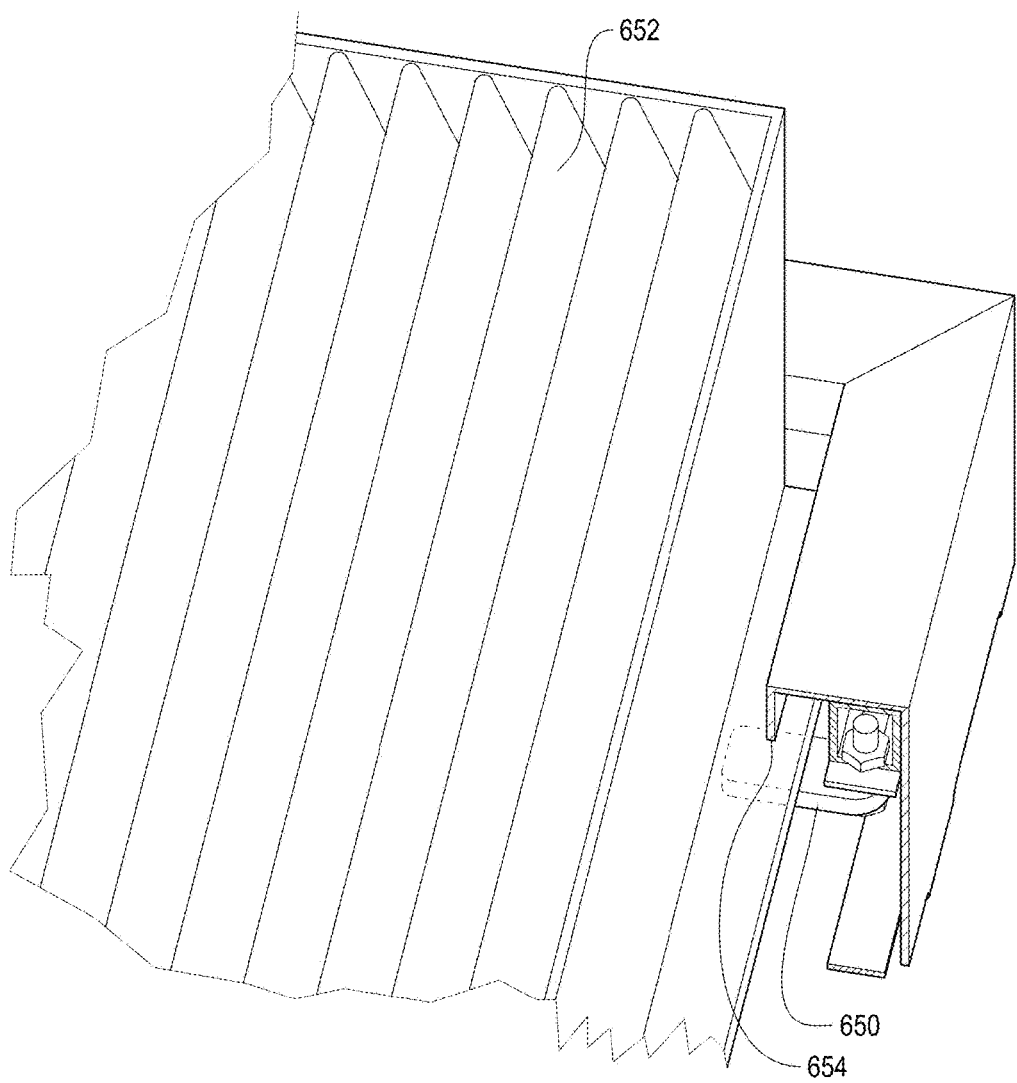
FIG. 25 is a perspective view of a module having a filter, according to an embodiment of the present disclosure.

As should be appreciated, the number and location of each of these modules may be varied as desired or needed, such as based on the particular application or environment. For example, a plurality of modules may be installed for a particular environment that includes easy load HEPA (see FIG. 25 showing a HEPA filter 652 locked into place with a HEPA lock 650 in combination with an airframe knife edge seal 654) and easy clean damper/diffuser features as described herein, such as using a hinged access configuration as described herein. Additionally, in some embodiments, single cell flex mount modules may be provided, which are configured like the structural mounts 610 and having bolt-on capabilities (e.g., bolt-on fastening or connection to another module, which allows for flexible and movable mounting locations and positions.

In various embodiments, multiple attachment points are provided per module (e.g., four attachment points per module). In these embodiments, anchoring installation time is reduced, which in some cases, is thirty times faster than conventional system installations.

Thus, as shown and described herein, various embodiments, including, for example, the supply air array 106 is configured to direct pressurized air underneath an entire lower surface of a frame structure that includes easily removable light assemblies. The pressurized air underneath the supply air array 106 reduces or eliminates turbulent recirculation of contaminants directly over the patient and surgical site. The air passages 450 direct air under the light housing 400 or any space between the airframe members 402. The pressurized air under the light housing 400 reduces or eliminates turbulent recirculation of air that might entrain contaminants.

Variations and modifications to the various embodiments are contemplated. For example, one or more of the structural elements or components of the embodiments described herein may be modified or additional elements provided, such as illustrated in FIGS. 26-33. The modifications shown relate generally to the airframe system 350 described herein. As should be appreciated, the components may be coupled together in different configurations as desired or needed, and as discussed herein.

Figure 26:
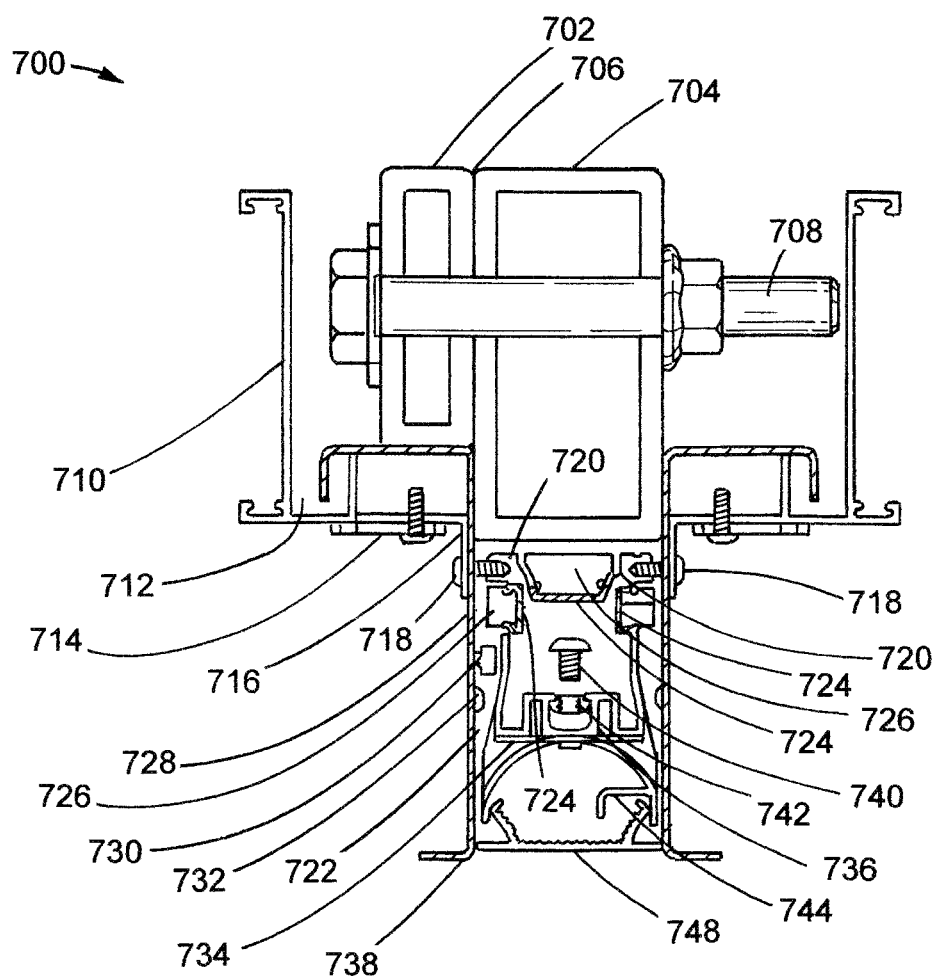
FIG. 26 illustrates a grid assembly, according to an embodiment of the present disclosure.
Figure 27:
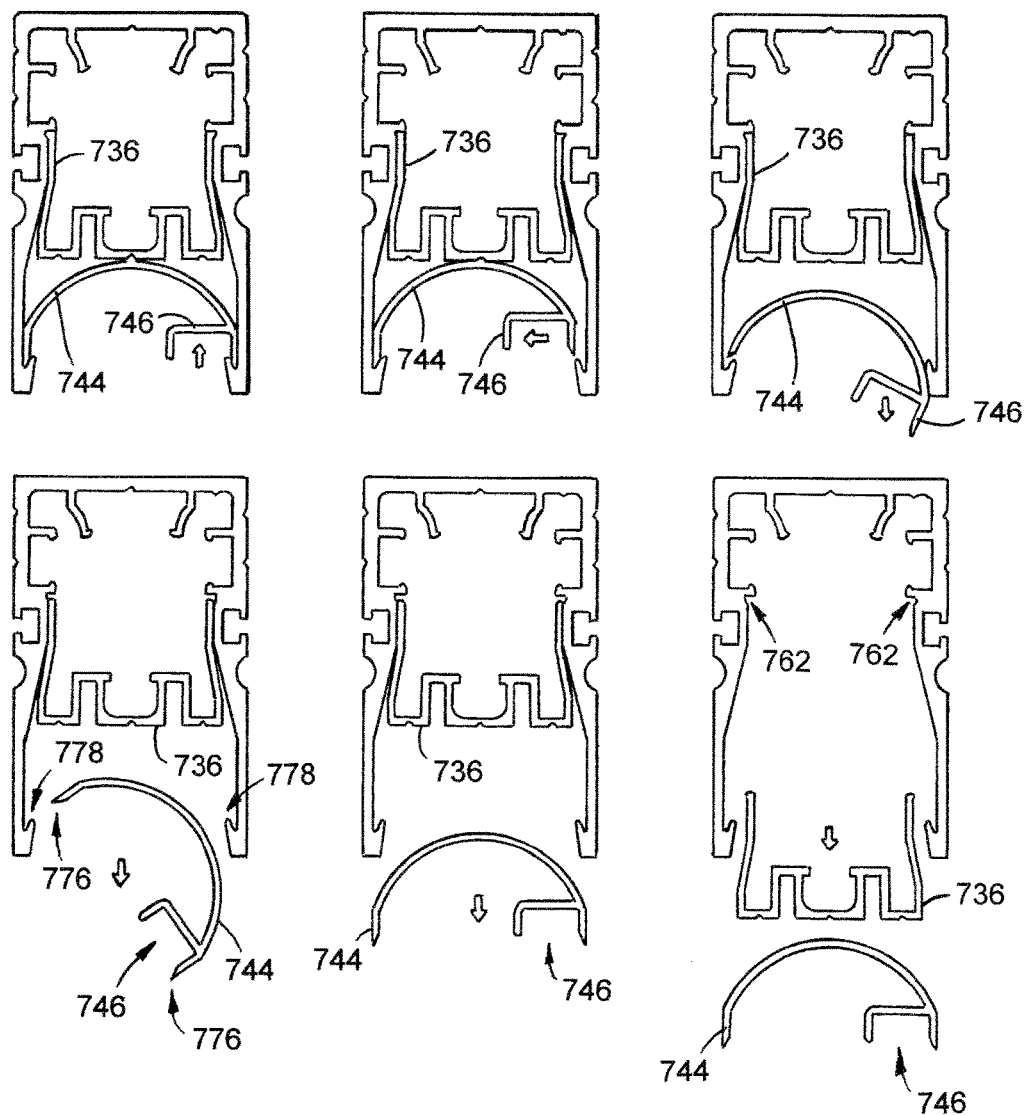
FIG. 27 illustrates an airframe grid and retainer clip, according to an embodiment of the present disclosure.

More particularly, FIG. 26 illustrates a full grid assembly 700 in accordance with an embodiment. The arrangement allows for easily installation and mounting of various components, such as coupling a lighting module to the structure of the assembly 700. The assembly 700 generally includes mounting, positioning and alignment components that facilitate the installation of the assembly in various embodiments. In the illustrated embodiment, the assembly 700 includes a support portion 702, which forms part of the support structure of the assembly. In one example, the support portion 702 is a support beam or tube, such as a Hollow Structural Section (HSS) tube. In some examples, the support portion 702 is metal (e.g., steel) having a hollow tubular cross-section. However, it should be appreciated that the support portion 702 can be sized and shaped differently. For example, the support portion 702 can be configured as an HSS member having different shapes, such as circular, square, rectangular or elliptical. It should be appreciated that different support structures or elements can be used, including support structures having different hollow configurations or non-hollow configurations.

In the illustrated embodiment, the support portion 702 is positioned at a perimeter of a module and may be embodiment, for example, as the HSS tube frame 302 described and illustrated herein. It should be noted that there is no light element under the support portion 702 in the illustrated example. The support portion 702 is configured to couple to (e.g., bolt through) to an adjacent module that has a light element. For example, the support portion 702 is coupled to a support portion 704 using a fastener, illustrated as a bolt 708. The support portion 704 in one example is another HSS member, illustrated as an HSS tube. In the illustrated configuration, the support portion 704 is larger than the support portion 702, both in width and height. The dimension of the support portions 702 and 704 may be varied as desired or needed and the relative dimensions are shown as an example. In one configuration, the support portion 702 is a 1×3 HSS tube and the support portion 704 is a 2×4 HSS tube. The support portions 702 and 704 define a support structure for the assembly 700 and include a seam 706 (module seam) therebetween. In one example, the support portion 704 includes a light element thereunder, such that in a grid arrangement, at one or more seams 706, one side includes a light element and the other side does not include a light element.

The assembly 700 also includes an air filter frame, illustrated as a HEPA filter frame 710. The HEPA filter frame 710 is configured to receive therein and/or house a HEPA filter media. It should be appreciated that different filter elements may be used as desired or needed, such as based on filtering requirements. In one example, the HEPA filter media is installed in the system to filter out contaminants. For example, the HEPA filter media is installed from below the assembly and lifted into place as described in more detail herein. In one example, is a gel filled trough 712 in the HEPA filter frame 710 seals to a knife edge track 728 once installed and as described in more detail herein. In one example, the knife edge track 728 is formed into a frame of four sides with a top that has been welded and sealed with caulking. The knife edge track 728 in the illustrated embodiment faces downward at the top of the frame and penetrates the gel (not shown) within the HEPA filter trough 712 in order to seal the system. In one configuration, a plurality of air passages is provided at the bottom of the track to allow air to be introduced under the light grid at a 45 degree angle as described in more detail herein.

The HEPA filter media is held in place with a plurality of filter locks 714, which in one embodiment includes four HEPA locks. The filter locks 714 in one example have a length greater than a width and are operable to rotate to lock and unlock the HEPA filter media. For example, the filter locks 714 are rotatable ninety degrees in one example to swing under the HEPA filter media once in place to hold the HEPA filter media in position.

The filter support arrangement further includes a filter lock angle 716, illustrated as corner support that holds the filter locks 714 to the assembly 700. In one example, the filter lock angle 716 is secured to the assembly using fasteners, such as screws 718. Thus, the filter lock angle 716 is screwed to the assembly 700 in some examples using sheet metal screws (e.g., screw the filter lock angle 716 into the airframe grid described herein). As can be seen, the screws 718 are shielded by a wireway channel leg 720 to prevent any wires running through the grid defined by the assembly 700 from getting cut by the screw 718. Thus, in the illustrated example, the wireway channel leg 720 provides a boundary for the sheet metal screw 718 in order to protect the wiring within an airframe grid 722. The wireway channel leg 720 also provides a wall that creates a wireway channel 726 allowing for a snap in channel cover clip, illustrated as a wireway channel cover clip 724 to enclose the wires (not shown) therein.

In one example, the wireway channel cover clip 724 defines a profile that can snap into the wireway channel 726 in order to enclose a wire or group of wires therein. The wireway channel cover clip 724 acts as a boundary between the wires in the channel and other wires within the system. The wireway channel cover clip 724 in one example is configured as a cover and runs the full length of the airframe grid 722 to fully enclose the wires within. As another example, the wireway channel cover clip 724 cab be cut into smaller pieces to hold the wire in place, thereby defining a clip structure. The airframe grid 722 in various examples is configured to house all the wiring and lighting components. The airframe grid 722 (configured in some embodiments as a light bar) also acts as a fixing element to attach the structural framing and the knife edge track 728 thereto.

It should be appreciated that additional wireway channel cover clips 724 can be provided to cover other wireway channels 726, such as along sides of the structure as shown in FIG. 26. In the illustrated embodiment, the wireway channels 726 are longitudinally extending channels and can be sized and shaped as desired or needed. In the illustrated embodiment, three wireway channels 726 are shown that allow for wires to run therethrough without interference from other components placed into the system. The three wireway channels 726 in one example allow for separation of high voltage, low voltage, control signal, audio, video or other wiring circuits.

The assembly 700 further includes a rivet track 730 extending along an outside surface of the airframe grid 722. In the illustrated embodiment, the rivet track 730 is configured to allow for attachment of the knife edge track 728 (illustrated as an airframe knife edge track) to the grid 722 or for other components such as a perimeter angle. Additionally, in one example, a seal track 732 (extending along an outside surface of the airframe grid 722) allows for either a wet or dry seal to be applied prior to assembly. The seal track 732 helps to prevent leaking of contaminants after assembly.

The assembly 700 also includes a lighting element 734 in one configuration. In one particular example, the lighting element an LED board or module that provides lighting thereunder (e.g., lights a space below). In one embodiment, the lighting element is coupled to a strut 736, illustrated as an LED strut, with fasteners, such as screws that penetrate into a screw boss in the strut 736. This arrangement is configured to keep the screws from engaging any wiring directly, which could strip the wire and cause a short. This arrangement also allows for a faster assembly of the components.

With respect to the strut 736, this component is configured in the illustrated example to provide several functions. In particular, the strut 726 is the primary attachment method for the lighting components. The lighting element 734 is screwed to the strut 736. Additionally, the lighting drivers, such as the LED drivers can also be screwed to the strut 736. The strut 736 in one example is formed with threads in the extrusion so that the lighting element 734 (e.g., LED board) is easily screwed down thereto. The above-described design also allows for several widths of the lighting element 734 (e.g., the LED board) to be used, with a second set of channels to receive a screw and protect the wiring from the sharp threads on the screw. It should be noted that the serpentine shape of the strut 736 allows the strut 736 to act as a heat sync due to the increased surface area in contact with the surrounding air space. This configuration allows heat to dissipate more efficiently and keeps the LED components cooler. As a result, heat buildup is reduced that can provide a safety feature and increased operating life of the LED lighting product.

In one example, airflow equalization passages 738 are provided as a plurality of penetrations at the lower edge of the knife edge track 728. The airflow equalization passages 738 are configured to allow air to be introduced under the light grid at a 45 degree angle. This configuration provides for pressure under the light in order to reduce turbulence in the air stream as described in more detail herein.

The assembly 700 in various embodiments allows for quick and easy coupling of the various components. For example, a bolt, illustrated as a T-nut bolt 740 screws into a T-nut 742 and fastens components to the system quickly and easily. In the illustrated embodiment, the T-nut 742 is a spring T-nut configured to allow placement of the T-nut bolt 740 within a T-nut slot 750 from the top with both ends of the slot captured. This coupling arrangement in various embodiments can be provided with or without the spring. The spring, when included, holds the T-nut 742 in place during assembly.

Figure 28:
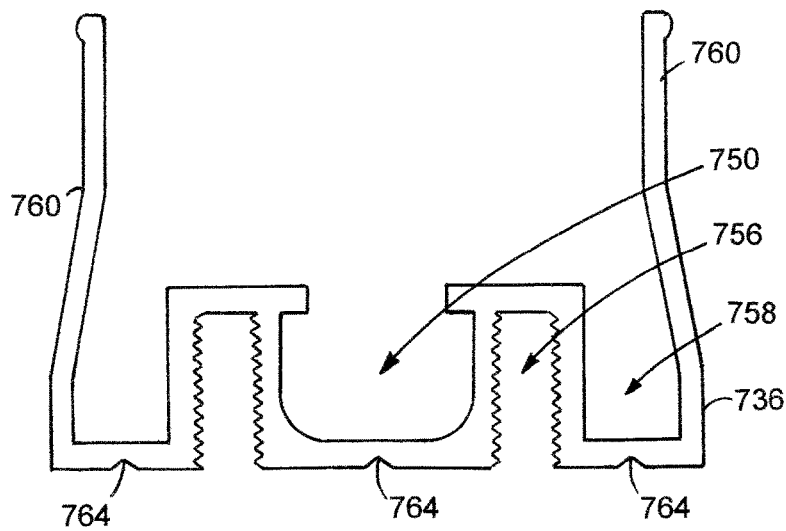
FIGS. 28 and 29 illustrate a strut, according to an embodiment of the present disclosure.
Figure 29:
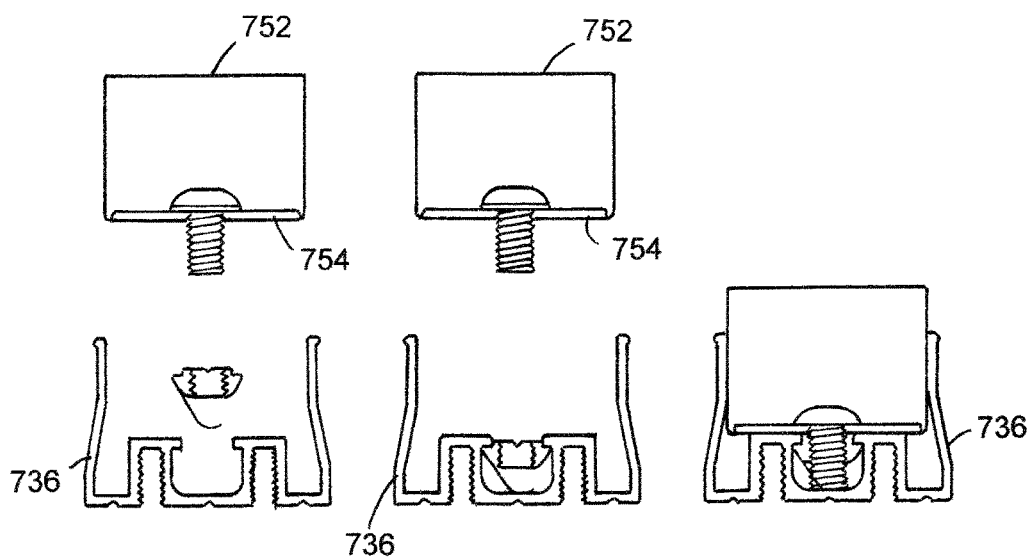
Figure 30:
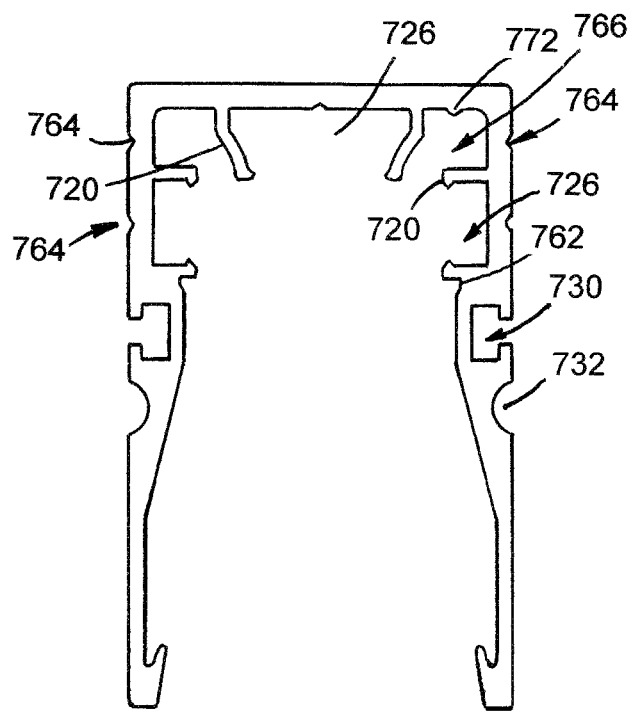
FIG. 30 illustrates an airframe grid, according to an embodiment of the present disclosure.

As can be seen more clearly in FIGS. 28 and 29, the strut 736 is easily installed and removed into the airframe grid 722. The strut 736 in one example is formed of metal (that acts as grounding in various embodiments) and configured to house an LED driver 752, as well as hold an LED lighting board 754 in the proper position. The strut 736 in one example has a serpentine shape allowing for increased surface area in contact with the surrounding air. As discussed herein, this configuration allows for the dissipation of heat from the airframe grid cavity. In one example, there are two types of screw channels. One screw channel 756 has threads and the other screw channel 758 does not have threads. These channels 756 and 758 allow for the installation of different sized boards 754, such as having two different sizes. The threaded channel 756 is configured to couple with a machine screw and the non-threaded channel 758 is configured to couple with a self-tapping metal screw, in some embodiments. Both channels 756 and 758 are configured in various examples to protect the wiring in the strut 736 from the sharp screw threads.

The T-Nut slot 750 is configured to allow fast and easy installation of the driver components into the strut 736 as described herein. The T-nut 742 (with or without spring) is installed into the slot 750 from the top and includes a threaded hole for bolting. The driver 752 is installed from the top and two screws are installed at each end into the T-nut 742. The strut 736 is then pushed into the airframe grid 722 until top legs 760 register with a snap fit into a registration groove 762 (illustrated in FIGS. 27 and 30) into the grid 722. A retainer clip 744 is then installed to hold the strut 736 into place as described below.

It should be noted that the strut 736 includes a plurality of center finders 764 that allow for easier identification of center positions for installing screws of other fastening mechanisms. It should be noted that additional center finders 764 may be provide and located in different positions along any portion of the strut 736. Additionally, fewer center finders 736 also may be provided. Also, while the center finders 764 are illustrated as triangular indents, different sized and shaped features may be provided.

In particular, in one example, the retainer clip 744 is arcuate or curved shaped, such as crescent shaped, so that the retainer clip 744 can be installed and removed easily without any tools as described in more detail herein. The use of the retainer clip 744 in this assembly requires no tools or hardware to install or remove the lighting components, such as the LED lighting components. In the illustrated example, the retainer clip 744 includes a release member, illustrated as a thumb press lever 746 (as seen more clearly in FIG. 27) on the inside portion of the retainer clip 744. In operation, when the retainer clip 744 is pushed (such as by applying a force thereto) as shown by the arrows in FIG. 27, the retainer clip 744 is released to allow removal thereof, as well as access to components there-above. As can be seen, ends 776 of the retainer clip 744 are configured to engage grooves 778 in the airframe grid 722.

In one embodiment, the retainer clip 744 is formed from a flexible material that can spring into place (e.g., allows biasing). For example, the retainer clip 744 in some embodiment is formed from a plastic or plastic composite material. It should be noted that the retainer clip 744 is shown coupled to the assembly 700, but may be used in other applications and with other structural support assemblies to provide a retaining feature.

The retainer clip 744 is designed in one example with the thumb press lever 746 being an integral L-shaped thumb tab. The thumb press lever 746 is used to apply pressure and grab the clip from below in order to remove thumb press lever 746.

Figure 31:
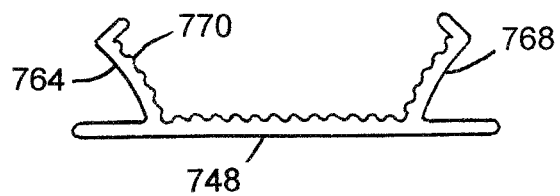
FIG. 31 illustrates a light lens, according to an embodiment of the present disclosure.
Figure 32:
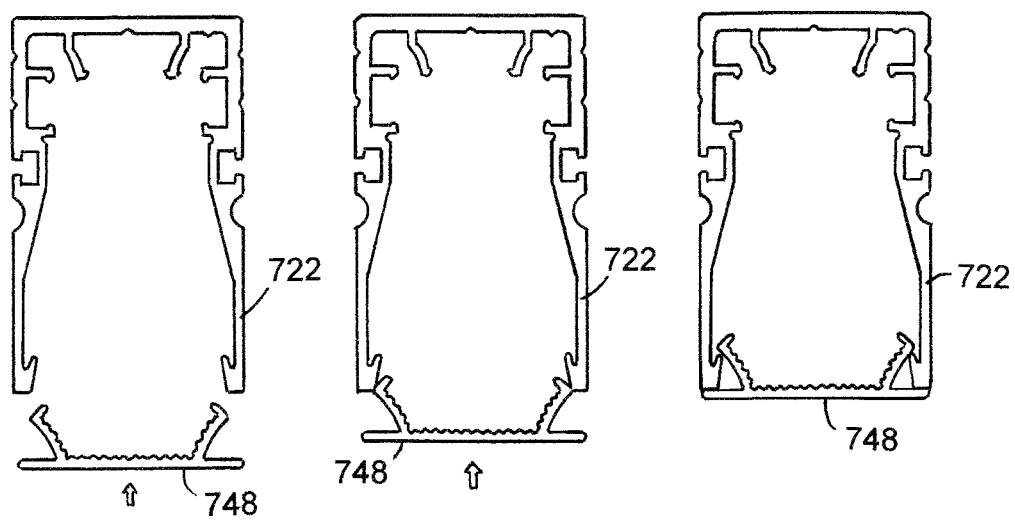
FIG. 32 illustrates an airframe grid and light lens, according to an embodiment of the present disclosure.
Figures 33A, 33B:
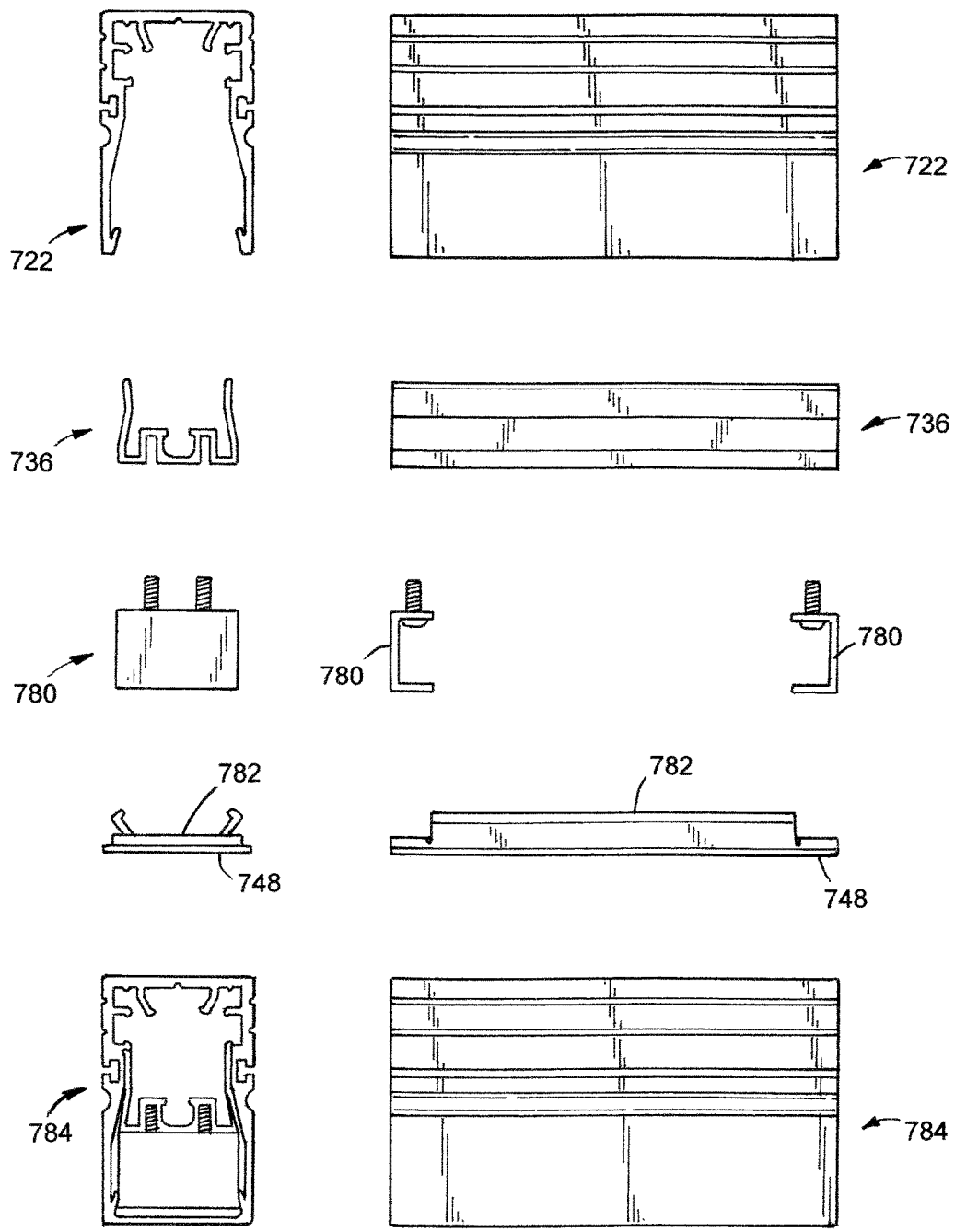
FIGS. 33A and 33B illustrate a sealing arrangement, according to an embodiment of the present disclosure.
Figure 34:
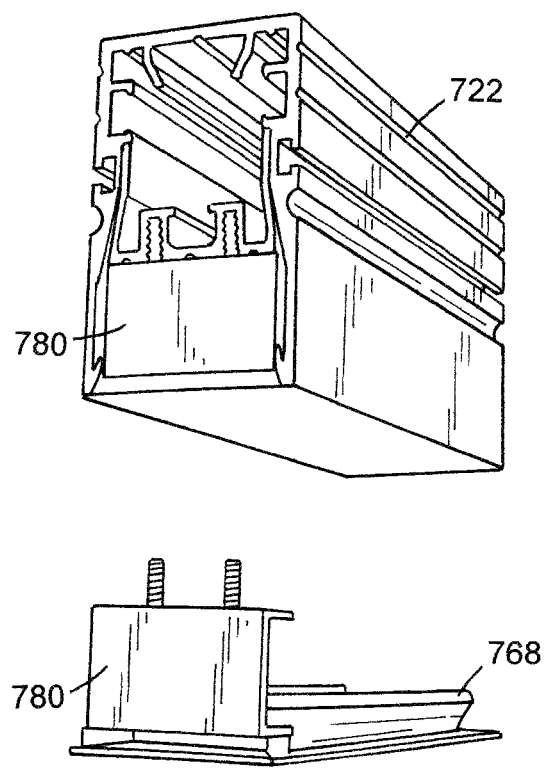
FIG. 34 illustrates a gasket channel, according to an embodiment of the present disclosure.
Figure 35:
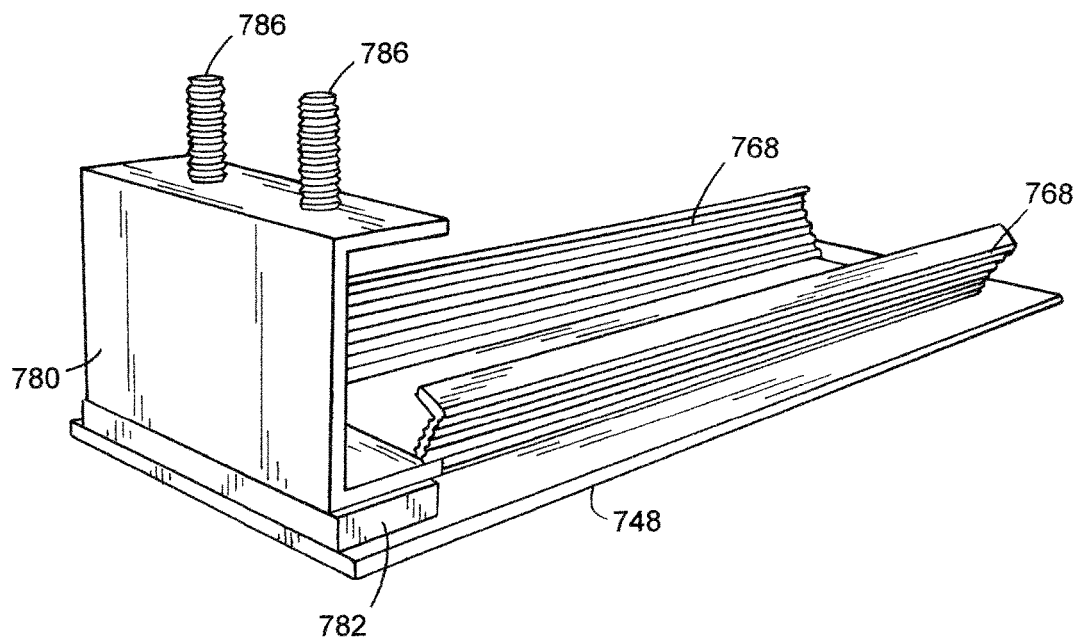
FIG. 35 illustrates a gasket channel and a light lens gasket, according to an embodiment of the present disclosure.

As can be seen more clearly in FIGS. 31 and 32, the grid 722 is shaped to include various wireway channels 726, as well as other channels. For example, a screw track 766 is provided that allows for a screw to penetrate the side of the grid 722, such as through the center finder 764. It should be noted that in some embodiments other features located in positions other than the center can be provided to facilitate fastening connections. For example, additional or different registration bumps may be provided as desired or needed.

The assembly 700 includes a light lens 748 that is removably coupled to the assembly 700. In one example, the light lens 748 closes the system to reduce dust and water ingress and provides light diffusion in order to reduce glare, but allows an increased or the highest light output from the grid. As can be seen in FIG. 31, the light lens 748 includes retaining wings 768 that are bendable or compressible to allow for removable coupling of the light lens 748 to the grid 722 as illustrated in FIG. 32. Additionally, the light lens 748 includes a plurality of ribs 770, configured as diffusion ribs along an inner surface of the light lens 748. The ribs 770 in one embodiment extend along the entirety of the bottom of the light lens 748 (as viewed in FIG. 31) and along the retaining wings 768.

It should be noted that additional features may be provided. For example, as shown more clearly in FIG. 30, a registration feature, illustrated as a registration bump 772 is provided at a top portion of the airframe grid 722. In some embodiment, the location and/or shape and/or number of the registration bumps 772 acts as an identifier of the particular configuration of the airframe grid 722.

As other examples, a sealing arrangement can be provided as illustrated in FIGS. 33A, 33B, 34 and 35. More particularly, the sealing arrangement in one example includes a gasket channel 780 and the light lens 748 with a gasket 782. In this embodiment 736, when the elements are coupled together, a sealed assembly 784 is provided. In particular, the gasket channel 780 and gasket 782 seal the light lens 748. As can be seen more clearly in FIGS. 34 and 35, the gasket channel 780 in one embodiment includes bolts 786 extending from a top of the gasket channel 780 that allow for coupling to the strut 736.

Figure 36:
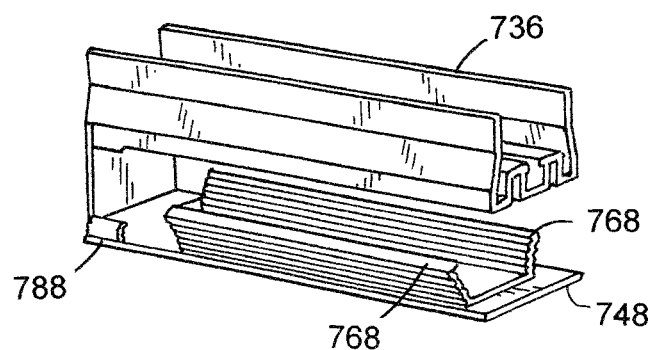
FIGS. 36 and 37 illustrate different positioning arrangements of the gasket channel, according to embodiments of the present disclosure.
Figure 37:
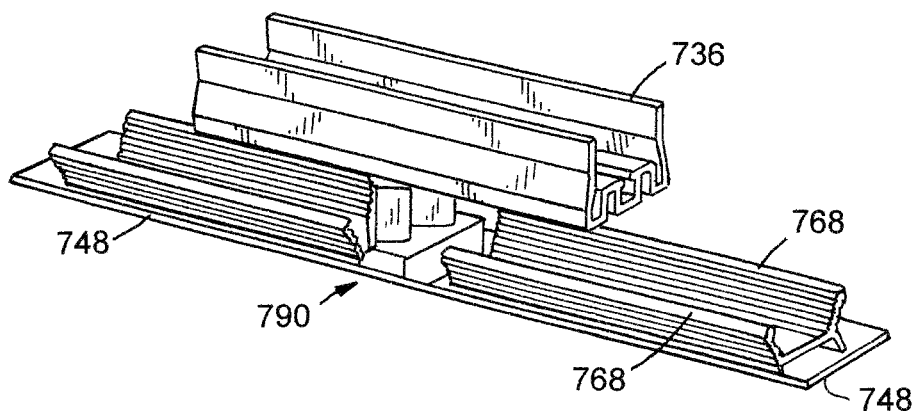

The gasket channel 780 and gasket 782 can have different shapes and sizes, as well as be formed from different materials. For example, the gasket channel 780 in one example is general C-shaped and covers an end of the sealed assembly 784, as can be seen more clearly in FIG. 36. That is, the gasket channel 780 is positioned at an end 788 of the light lens 748. In some embodiments, the gasket channel 780 can additionally or alternatively be positioned at a seam 790 between two light lenses 748.

Figure 38:
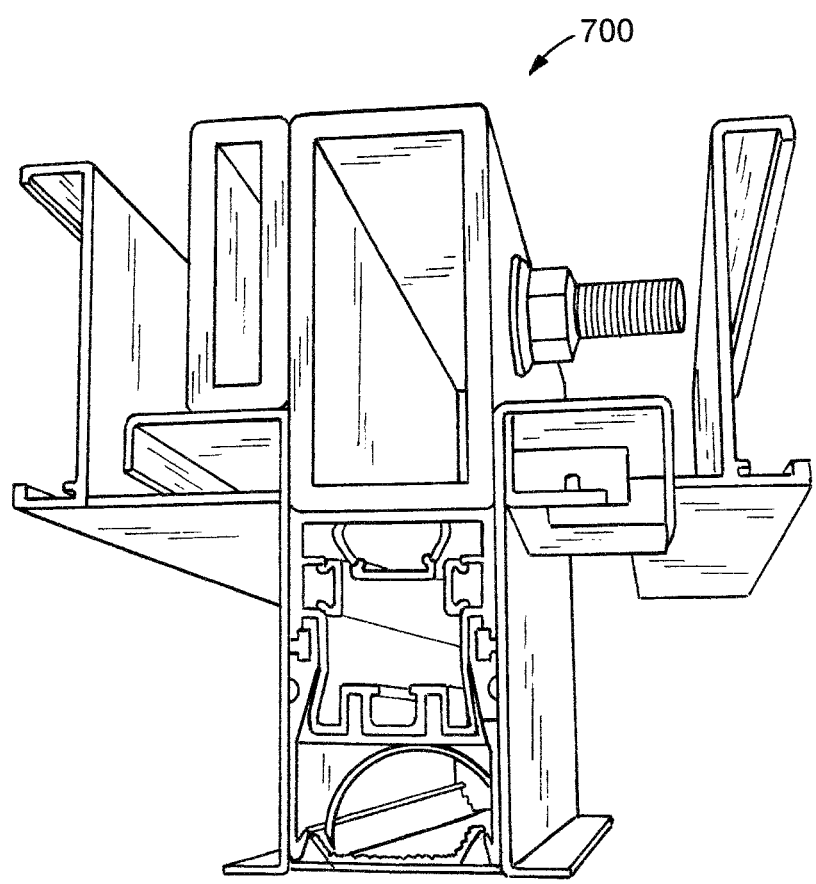
FIG. 38 illustrates a grid assembly, according to an embodiment of the present disclosure.

Thus, the assembly 700 that is easier to install and maintain can be provided, such as illustrated in FIG. 38.

Embodiments may be used in relation to a hospital operating room environment. Optionally, embodiments of the present disclosure may be used in various other settings in which pressurized airflow may be directed in combination with ceiling mounted equipment and/or lighting assemblies. For example, embodiments of the present disclosure may be used in dental offices, manufacturing clean rooms, residential spaces, and the like. Additionally, it should also be appreciated that one or more air filtering, air sterilizing and/or air purifying devices or methods may be used in combination with each other, for example, in a multi-stage cleaning design to cleanse the air and/or surfaces through which the air passes.

For example, in various embodiments, the air cleansing device may be an air sterilizing device. The air sterilizing device may be any type of device that effects a sterilization of the air flow, which may include introducing or adding a cleansing or sterilizing agent or chemical into the air flow path. Thus, the air sterilizing device in various embodiments removes or changes the material properties of the contaminants or air particles to sterilize the air flow that is thereafter delivered as discussed herein. For example, the air sterilizing device may inject a cleansing or sterilizing agent or chemical into the air flow path that not only sterilizes or sanitizes the air, but also sterilizes or sanitizes the surfaces through which the air flows. It should be noted that any type of sterilizing or sanitizing method may be performed by the air sterilizing device, which in some embodiments may include using non-chemical methods to perform the sterilizing or sanitizing.

As another example, the air cleansing device may be an air purifying device. The air purifying device may be any type of device that purifies the air flow. Thus, the air purifying device in various embodiments changes the material properties of the contaminants or air particles to purify the air flow that is thereafter delivered as discussed herein. For example, the air purifying device may use one or more air ionization processes to purify the air flow, which can also effect a cleansing or purifying of the surfaces through which the air flows. It should be noted that any type of purifying method may be performed by the air purifying device, which in some embodiments may include using non-ionization methods to perform the sterilizing or sanitizing (e.g., different types of UV lights and catalysts).

It should be appreciated that any air purifying device may be used in or with one or more embodiments. For example, in one or more embodiments, any type of air purifying device that removes contaminants and sanitizes both the air and surfaces may be used. In some embodiments, the air purifying device is any device used to kill, render impotent or reduce bacteria, viruses, mold, fungi, allergens, VOCs, etc. Some examples of the air purifying device include, but are not limited to ultraviolet (UV) light, vaporized hydrogen peroxide (VHP), nano technology, ionization, bi-polar ionization, hydroxyl radicals, hydroperoxides, etc.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An air frame system comprising:
   a frame body defining one or more openings;
   a plurality of air passages along an inner periphery of the one or more openings;
   an airframe grid coupled to the frame body, the airframe grid comprising at least one wireway channel therein;
   a wireway channel cover clip removably coupled to the at least one wireway channel;
   a light assembly removably coupled to the airframe grid;
   a strut removably coupled inside the airframe grid wherein the airframe grid comprises a registration groove for receiving therein an end of the strut; and
   a retainer clip removably coupled to the airframe grid, the retainer clip retaining the light assembly within the airframe grid.

2. The air frame system of claim 1, the retainer clip being arcuate shaped and bendable, the retainer clip further comprising a press lever configured to release the retainer clip from the airframe grid upon pressure being applied thereto.

3. The air frame system of claim 2, wherein the press level comprises an L-shaped thumb tab.

4. The air frame system of claim 1, further comprising a light lens removably coupled to the airframe grid and covering an access opening of the airframe grid, the light lens comprising diffusion ribs along an inner surface thereof, including along a bottom surface and side surfaces.

5. The air frame system of claim 1, further comprising a light lens removably coupled to the airframe grid and covering an access opening of the airframe grid, the light lens comprising a gasket along an inner surface thereof.

6. The air frame system of claim 1, further comprising a light lens removably coupled to the airframe grid and covering an access opening of the airframe grid, and a gasket channel coupled to an end of the light lens covering a side opening of the light lens.

7. The air frame system of claim 1, wherein the strut comprises at least one threaded screw channel and at least one non-threaded screw channel.

8. The air frame system of claim 1, wherein the strut comprises a nut slot therein.

9. The air frame system of claim 1, wherein the strut is serpentine shaped.

10. The air frame system of claim 1, wherein the airframe grid further comprises a rivet track and a seal track extending along an outside surface thereof.

11. The air frame system of claim 1, wherein the light assembly is removably coupled to the airframe grid without tools.

12. The airframe system of claim 1, wherein airframe grid is configured to be coupled to a Hollow Structural Section (HSS) tube.

13. An air frame system comprising:
   a frame body defining one or more openings;
   a plurality of air passages along an inner periphery of the one or more openings;
   an airframe grid coupled to the frame body, the airframe grid comprising at least one wireway channel therein;
   a wireway channel cover clip removably coupled to the at least one wireway channel;
   a light assembly removably coupled to the airframe grid;
   a light lens removably coupled to the airframe grid and covering an access opening of the airframe grid, the light lens comprising a gasket along an inner surface thereof; and
   a retainer clip removably coupled to the airframe grid, the retainer clip retaining the light assembly within the airframe grid.

14. The air frame system of claim 13, wherein the light lens comprises diffusion ribs along an inner surface thereof, including along a bottom surface and side surfaces.

15. The air frame system of claim 13, further comprising a gasket channel coupled to an end of the light lens covering a side opening of the light lens.

16. The airframe system of claim 13, wherein airframe grid is configured to be coupled to a Hollow Structural Section (HSS) tube.

17. The airframe system of claim 13, further comprising a strut removably coupled inside the airframe grid wherein the airframe grid comprises a registration groove for receiving therein an end of the strut.

18. An air frame system comprising:
   an airframe grid comprising at least one wireway channel therein, wherein the airframe grid further comprises a rivet track and a seal track extending along an outside surface thereof, the rivet track shaped to receive at least a portion of a rivet therein;
   a wireway channel cover clip removably coupled to the at least one wireway channel;
   a light assembly removably coupled to the airframe grid; and
   a retainer clip removably coupled to the airframe grid, the retainer clip retaining the light assembly within the airframe grid.

19. The airframe system of claim 18, wherein airframe grid is configured to be coupled to a Hollow Structural Section (HSS) tube.

20. The airframe system of claim 18, further comprising a strut removably coupled inside the airframe grid wherein the airframe grid comprises a registration groove for receiving therein an end of the strut.

* * * * *